United States Patent [19]

Van Ooijen et al.

[11] Patent Number: 5,593,963
[45] Date of Patent: Jan. 14, 1997

[54] EXPRESSION OF PHYTASE IN PLANTS

[75] Inventors: Albert J. J. Van Ooijen, Voorburg; Krijn Rietveld, Vlaardingen; Andreas Hoekema, Oegstgeest; Jan Pen, Leiden; Peter C. Sijmons, Amsterdam; Teunis C. Verwoerd, Leiden, all of Netherlands

[73] Assignees: Mogen International, Leiden; Gist-brocades, B.V., Delft, both of Netherlands

[21] Appl. No.: 146,424

[22] Filed: Nov. 2, 1993

Related U.S. Application Data

[63] Continuation-in-part of Ser. No. 756,864, Sep. 11, 1991, abandoned, which is a continuation-in-part of Ser. No. 586,765, Sep. 21, 1990, abandoned.

[30] Foreign Application Priority Data

Mar. 25, 1991 [EP] European Pat. Off. ............ 91200687

[51] Int. Cl.[6] .................... A61K 38/46; C12N 15/83; A01H 5/00; A23K 1/165
[52] U.S. Cl. .................... 514/12; 435/320.1; 435/69.1; 435/69.8; 435/196; 435/252.3; 435/240.4; 435/172.3; 514/44; 426/53; 426/54; 426/635; 424/93.21; 800/205; 800/250; 800/255; 536/24.1; 536/23.74
[58] Field of Search .................... 800/205, 250, 800/255; 435/320.1, 172.3, 41, 69.1, 69.8, 196, 240.4, 252.3; 536/24.1, 23.7, 23.74; 424/93.21; 426/53, 54, 635; 514/12, 44

[56] References Cited

U.S. PATENT DOCUMENTS

| | | | |
|---|---|---|---|
| 3,297,548 | 1/1967 | Ware et al. | 435/196 |
| 4,116,770 | 9/1978 | Goering et al. | 195/63 |
| 4,859,486 | 8/1989 | Douglass | 426/629 |

FOREIGN PATENT DOCUMENTS

| | | |
|---|---|---|
| 0380343 | 8/1980 | European Pat. Off. . |
| 0120516 | 10/1984 | European Pat. Off. . |
| 0159418 | 10/1985 | European Pat. Off. . |
| 0179441 | 4/1986 | European Pat. Off. . |
| 0176112 | 4/1986 | European Pat. Off. . |
| 0224287 | 6/1987 | European Pat. Off. . |
| 0249432 | 12/1987 | European Pat. Off. . |
| 0255378 | 2/1988 | European Pat. Off. . |
| 0287152 | 10/1988 | European Pat. Off. . |
| 0318341 | 5/1989 | European Pat. Off. . |
| 0321004 | 6/1989 | European Pat. Off. . |
| 0346909 | 12/1989 | European Pat. Off. . |
| 0420358 | 4/1991 | European Pat. Off. . |
| 2505594 | 2/1974 | Germany . |
| 262041 | 11/1988 | Germany . |
| 275704 | 1/1990 | Germany . |
| WO87/00865 | 2/1987 | WIPO . |
| WO87/07299 | 12/1987 | WIPO . |
| WO89/03887 | 5/1989 | WIPO . |
| WO89/05859 | 6/1989 | WIPO . |
| WO89/12386 | 12/1989 | WIPO . |
| WO90/01551 | 2/1990 | WIPO . |
| WO90/02484 | 3/1990 | WIPO . |
| WO90/09436 | 8/1990 | WIPO . |
| 9010076 | 9/1990 | WIPO .................... C12N 15/82 |

OTHER PUBLICATIONS

B. J. C. Cornelissen et al. Nature, vol. 321 (29 May '86) pp. 531–532.
T. Ohtani et al. Plant Mol. Biol., vol. 16 ('91) pp. 117–128.
B. Larkins et al. J. Cell Biochem, vol. Suppl. O (9 Part C) p. 264.
J. Sambrook et al., *Molecular Cloning—A Lab. Manual*, CSHL Press, 1989, pp. 11.2–11.19, 11.45–11.49, 11.52–11.61.
K. Ehrlich et al. Biochemical & Biophysical Research Communications, vol. 195 #1 ('93) pp. 53–57.
R. Freedman Cell, vol. 57, (Jun. 30, 1989) pp. 1069–1072.
E. Mullaney Mycologia, vol. 85(1) pp. 71–73 (1993).
Altenbach et al., "Enhancement of the methionine content of seed proteins by the expression of a chimeric gene encoding a methionine-rich protein in transgenic plants" *Plant Mol. Biol.* (1989) 13(5):513–522.
Barker et al., "Cellular localization of soybean storage protein messenger RNA in transformed tobacco seeds" *Proc. Natl. Acad. Sci. USA* (1988) 85(2):458–462.
Bustos et al., "Regulation of beta glucuronidase expression in transgenic tobacco plants by an adenosine thymidine–rich cis–acting sequence found upstream of a french bean beta phaseolin gene" *Plant Cell* (1989) 1(9):839–854.
Casey et al., "The structure of plant storage protein genes" *Plant Mol. Biol. Reporter* (1987) 5(2):261–281.
Christen et al., "Cloning of the phytase gene from germinating soybeans" *J. Cell Biochem.* (1988) Supplement 12, Part C, p. 190, (abstract No. L402).
Ellis et al., "Tissue–specific expression of a pea legumin gene in seeds of *Nicotiana plumbaginifolia*" *Plant Mol. Biol.* (1988) 10(3):203–214.
Gibson et al., "Phytase expression during seed germination" *J. Cell Biochem.* (1988) Supplemental 12, Part C, p. 192 (abstract No. L407).
Higgins et al., "The sequence of a pea vicilin gene and its expression in transgenic tobacco plants" *Plant Mol. Biol.* (1988) 11(5):683–696.

(List continued on next page.)

*Primary Examiner*—David T. Fox
*Assistant Examiner*—Charles C. P. Rories
*Attorney, Agent, or Firm*—Morrison & Foerster LLP

[57] ABSTRACT

The present invention provides for the expression of phytase in transgenic plants or plant organs and methods for the production of such plants. DNA expression constructs are provided for the transformation of plants with a gene encoding phytase under the control of regulatory sequences which are capable of directing the expression of phytase. These regulatory sequences include sequences capable of directing transcription in plants, either constitutively, or stage and/or tissue specific, depending on the use of the plant or parts thereof. The transgenic plants and plant organs provided by the present invention may be applied to a variety of industrial processes either directly, e.g. in animal feeds or alternatively, the expressed phytase may be extracted and if desired, purified before application.

13 Claims, 13 Drawing Sheets

OTHER PUBLICATIONS

Hoffman et al., "Synthesis and protein body deposition of maize 15-kD zein in transgenic tobacco seeds" *EMBO J.* (1987) 6(11):3213–3222.

Iturriaga et al., "Endoplasmic reticulum targeting and glycosylation of hybrid proteins in transgenic tobacco" *Plant Cell* (1989) 1:381–390.

Krebbers et al., "Production of peptides in plant seeds" *Trends in Biotechnol.* (1990) 8(1):1–3.

Shotwell et al., In: *The Biochemistry of Plants*, vol. 15, Stumpf, P. K. & Conn, E. E., eds. (Academic Press, San Diego, 1989), chap. 7, pp. 297–345.

Sijmons et al., "Production of correctly processed human serum albumin in transgenic plants" *Biotechnology* (1990) 8(3):217–221.

Vandekerckhove et al., "Enkephalins produced in transgenic plants using modified 2S seed storage proteins" *Biotechnology* (1989) 7:929–932.

Voelker et al., "In–vitro mutated phytohemagglutinin genes expressed in tobacco seeds: role of glycans in protein targeting and stability" *Plant Cell* (1989) 1(1):95–104.

Derwent Publication "Alerting Abstracts Bulletin", Abstract No. 90–210631/28, which abstracts DDR application 23.09.88–DD–320082 (31 Jan. 1990).

Han et al., "Phytate hydrolysis in soybean and cottonseed meals by *Aspergillus ficuum* phytase" *J. Agric. Food Chem.* (1988) 36(2):259–262.

Han, Y. W., "Removal of phytic acid form soybean and cottonseed meals" *J. Agric. Food Chem.* (1988) 36(6):1181–1183.

*Patent Abstracts of Japan* vol. 9, No. 17, (C–262) [1740] Jan. 24, 1985.

Jordano et al., "A sunflower helianthinin gene upstream sequence ensemble contains an enhancer and sites of nuclear protein interaction" *Plant Cell* (1989) 1(9):855–866.

Hesselman et al., "The effect of β–glucanase on the utilizaton of starch and nitrogen by broiler chickens fed on barley of low–or–high–viscosity" *Chem. Abstracts.* (1986) 105:574 (abstract No. 132749x).

Broz et al., "Effects of beta–glucanase on the feeding value of broiler diets based on barley or oats" *Chem. Abstracts* (1986) 105:569 (abstract No. 23478n).

Gopaldas et al., "Studies on a wheat–based amylase–rich food" *Food Science Technol. Abstracts* (1989) 21(8):123 (abstract 8 M 19).

Colot et al., "Localization of sequences in wheat endosperm protein genes which confer tissue-specific expression in tobacco" *EMBO J.* (1987) 6(12):3559–3564.

Ullah et al., "Extracellular phytase (E.C. 3.1.3.8) from *Aspergillus ficuum* NRRL 3135: purification and characterization" *Prep. Biochem.* (1987) 17(1):63–91.

Jähne et al., "Regeneration of fertile plants from protoplasts derived from embryogenic cell suspensions of barley" (*Hordeum vulgare* L.) *Plant Cell Reports* (1991) 10:1–6.

Gibson et al., "Purification and characterizaton of phytase from cotyledons of germinating soybean seeds" *Arch. Biochem. Biophys.* (1988) 260(2):503–513.

Abersold et al., "Internal amino acid sequence analysis of proteins separated by one– or two–dimensional gel electrophoresis after in situ protease digestion on nitrocellulase" *Proc. Natl. Acad. Sci. USA* (1987) 84:6970–6974.

Jaye et al., "Isolation of human anti–haemophilic factor IX cDNA clone using a unique 52–Base synthetic oligonucleotide probe derived from the amino acid sequence of bovine factor IX" *Nucl. Acids Res.* (1983) 11(8):2325–2335.

Dorel et al., "Transport of proteins to the plant vacuole is not by bulk flow through the secretory system, and requires positive sorting information" *J. Cell Biol.* (1989) 108:327–337.

Della–Chioppa et al., "Protein trafficking in plant cells" *Plant Physiol.* (1987) 84:965–968.

Hoffman et al., "A modified storage protein is synthesized, processed, and degraded in the seeds of transgenic plants" *Plant Mol. Biol.* (1988) 11:717–729.

Biosys Computer Database Abstract of Yang et al., "Purification and characterization of phytase from rat intestinal mucosa" *Biochem. Biophys. Acta* (1991) 1075(1):75–82. (Biosys No. 92122246).

Freedman et al., "Protein disulfide isomerase: multiple roles in the modification of nascent secretory proteins" *Cell* (1989) 57:1069–1072.

Perlman et al., "A putative signal peptidase recognition site and sequence in eukaryotic and prokaryotic signal peptides" *J. Mol. Biol.* (1983) 167:391–409.

von Heijne, G., "How signal sequences maintain cleavage specificity" *J. Mol. Biol.* (1984) 173:243–251.

Biosys Computer Database Abstract of Goel et al., "Multiple forms of phytase EC–3.1.3.8 in germinating cotyledons of *Cucurbita maxima*" *Phytochemistry* (1979) 18(12):1939–1942. (Biosys No. 70046645).

Biosys Computer Database Abstract of Pospisil et al., "The influence of humic acids on phytase activity isolated from wheat seeds" *Biol. Plant* (1975) 17(6):468–474. (Biosys No. 61051479).

Biosys Computer Database Abstract of Yoshida et al., "Phytase EC–3.1.3.8 activity associated with isolated aleurone particles of rice grains" *Agric. Biol. Chem.* (1975) 39(1):289–290. (Biosys No. 60051490).

Biosys Computer Database Abstract of Chan et al., "Distribution and properties of calcium atpase EC–3.6.1.3 phytase EC–3.1.3.8 and alkaline phosphatase EC–3.1.3.1 in isolated enterocytes from normal and vitamin D deficient rats" *Gut* (1983) 24(10):886–892. (Biosys No. 77085639).

Chrispeels, M. J., "Sorting of proteins in the secretory system" *Ann. Rev. Plant Physiol. Plant Mol. Biol.* (1991) 42:1–24.

John et al., "Reduction in the dietary bulk of soya–fortified bulgur wheat gruels with wheat–based amylase–rich food" *Food Science Technol. Abstracts* (1989) 21(12):124 (abstract No. 12 M 11).

```
  1 ATGGGCGTCTCTGCTGTTCTACTTCCTTTGTATCTCCTGTCTGGAGTCACCTCCGGACTG
-23   M  G  V  S  A  V  L  L  P  L  Y  L  L  S  G  V  T  S  G  L

61 GCAGTCCCCGCCTCGAGAAATCAATCCAGTTGCGATACGGTCGATCAGGGGTATCAATGC
      A  V  P  A  S  R  N  Q  S  S  C  D  T  V  D  Q  G  Y  Q  C
         -1 +1

121 TTCTCCGAGACTTCGCATCTTTGGGGTCAATACGCACCGTTCTTCTCTCTGGCAAACGAA
 18   F  S  E  T  S  H  L  W  G  Q  Y  A  P  F  F  S  L  A  N  E

181 TCGGTCATCTCCCCTGAGGTGCCCGCCGGATGCAGAGTCACTTTCGCTCAGGTCCTCTCC
 38   S  V  I  S  P  E  V  P  A  G  C  R  V  T  F  A  Q  V  L  S

241 CGTCATGGAGCGCGGTATCCGACCGACTCCAAGGGCAAGAAATACTCCGCTCTCATTGAG
 58   R  H  G  A  R  Y  P  T  D  S  K  G  K  K  Y  S  A  L  I  E

301 GAGATCCAGCAGAACGCGACCACCTTTGACGGAAAATATGCCTTCCTGAAGACATACAAC
 78   E  I  Q  Q  N  A  T  T  F  D  G  K  Y  A  F  L  K  T  Y  N

361 TACAGCTTGGGTGCAGATGACCTGACTCCCTTCGGAGAACAGGAGCTAGTCAACTCCGGC
 98   Y  S  L  G  A  D  D  L  T  P  F  G  E  Q  E  L  V  N  S  G

421 ATCAAGTTCTACCAGCGGTACGAATCGCTCACAAGGAACATCGTTCCATTCATCCGATCC
118   I  K  F  Y  Q  R  Y  E  S  L  T  R  N  I  V  P  F  I  R  S

481 TCTGGCTCCAGCCGCGTGATCGCCTCCGGCAAGAAATTCATCGAGGGCTTCCAGAGCACC
138   S  G  S  S  R  V  I  A  S  G  K  K  F  I  E  G  F  Q  S  T

541 AAGCTGAAGGATCCTCGTGCCCAGCCCGGCCAATCGTCGCCCAAGATCGACGTGGTCATT
158   K  L  K  D  P  R  A  Q  P  G  Q  S  S  P  K  I  D  V  V  I

601 TCCGAGGCCAGCTCATCCAACAACACTCTCGACCCAGGCACCTGCACTGTCTTCGAAGAC
178   S  E  A  S  S  S  N  N  T  L  D  P  G  T  C  T  V  F  E  D

661 AGCGAATTGGCCGATACCGTCGAAGCCAATTTCACCGCCACGTTCGTCCCCTCCATTCGT
198   S  E  L  A  D  T  V  E  A  N  F  T  A  T  F  V  P  S  I  R

721 CAACGTCTGGAGAACGACCTGTCCGGTGTGACTCTCACAGACACAGAAGTGACCTACCTC
218   Q  R  L  E  N  D  L  S  G  V  T  L  T  D  T  E  V  T  Y  L

781 ATGGACATGTGCTCCTTCGACACCATCTCCACCAGCACCGTCGACACCAAGCTGTCCCCC
238   M  D  M  C  S  F  D  T  I  S  T  S  T  V  D  T  K  L  S  P
```

FIG.2A

```
 841 TTCTGTGACCTGTTCACCCATGACGAATGGATCAACTACGACTACCTCCAGTCCTTGAAA
 258  F  C  D  L  F  T  H  D  E  W  I  N  Y  D  Y  L  Q  S  L  K

901 AAGTATTACGGCCATGGTGCAGGTAACCCGCTCGGCCCGACCCAGGGCGTCGGCTACGCT
 278  K  Y  Y  G  H  G  A  G  N  P  L  G  P  T  Q  G  V  G  Y  A

961 AACGAGCTCATCGCCCGTCTGACCCACTCGCCTGTCCACGATGACACCAGTTCCAACCAC
 298  N  E  L  I  A  R  L  T  H  S  P  V  H  D  D  T  S  S  N  H

1021 ACTTTGGACTCGAGCCCGGCTACCTTTCCGCTCAACTCTACTCTCTACGCGGACTTTTCG
 318  T  L  D  S  S  P  A  T  F  P  L  N  S  T  L  Y  A  D  F  S

1081 CATGACAACGGCATCATCTCCATTCTCTTTGCTTTAGGTCTGTACAACGGCACTAAGCCG
 338  H  D  N  G  I  I  S  I  L  F  A  L  G  L  Y  N  G  T  K  P

1141 CTATCTACCACGACCGTGGAGAATATCACCCAGACAGATGGATTCTCGTCTGCTTGGACG
 358  L  S  T  T  T  V  E  N  I  T  Q  T  D  G  F  S  S  A  W  T

1201 GTTCCGTTTGCTTCGCGTTTGTACGTCGAGATGATGCAGTGTCAGGCGGAGCAGGAGCCG
 378  V  P  F  A  S  R  L  Y  V  E  M  M  Q  C  Q  A  E  Q  E  P

1261 CTGGTCCGTGTCTTGGTTAATGATCGCGTTGTCCCGCTGCATGGGTGTCCGGTTGATGCT
 398  L  V  R  V  L  V  N  D  R  V  V  P  L  H  G  C  P  V  D  A

1321 TTGGGGAGATGTACCCGGGATAGCTTTGTGAGGGGGTTGAGCTTTGCTAGATCTGGGGGT
 418  L  G  R  C  T  R  D  S  F  V  R  G  L  S  F  A  R  S  G  G

1381 GATTGGGCGGAGTGTTTTGCTTAG
 438  D  W  A  E  C  F  A  *
```

FIG.2B

Polylinker sequences:

| Eco RI | Kpn I | Sma I | Bam HI | Xba I | Xho I | Hind III |

5'GGAATTCTGGTACCTCCCGGGAGGATCCATCTAGAGCTCGAGTAAGCTTC 3'

Sac I

Oligonucleotide duplex A

```
                      NcoI           BamHI HindIII
5' GGGTTTTTATTTTTAATTTCTTTCAAATACTTCCACCATGGTAACGGATCCA   3'
3' CCCAAAAATAAAAATTAAAGAAAGTTTATGAAGGTGGTACCCATTGCCTAGGTTCGA 5'
```

Oligonucleotide duplex B

```
                                                                                    SphI XhoI BamHI
5' CATGAACTTCCTCAAGAGCTTCCCCTTTTATGCCTTCCTTGTTTTGGCCAATACTTTGTAGCTGTTACGCATGCTCGAG   3'
3'       TGAAGGAGTTCTCGAAGGGGAAAATACGGAAGGAACAAAACCGGTTATGAAACATCGACAATGCGTACGAGCTCCTAG 5'
```

Oligonucleotide duplex C

```
       SphI     XhoI                PstI  BamHI
5'      CT  CTGGCAGTCCCCGGCCTCGAGCCCCTGCAG   3'
3' GTACGA  GACCGTCAGGGGCCGGAGCTCGGGGACGTCCTAG 5'
   PROB12      Mature phytase
   signal
   peptide
```

FIG. 4A

Oligonucleotide duplex D

```
    NcoI              XhoI   EcoRV PstI   BglII         HindIII

HisGlySerThrAla|LeuAlaValProAlaSer
5' CATGGCTCTACAGCT    CTGGCAGTCCCCGCCTCGAGGATATCCTGCAGATCTCCCCA    3'
3'     CGAGATGTCGA    GACCGTCAGGGGCGGAGCTCCTATAGGACGTCTAGAGGGGTTCGA 5'
         CruA signal       Mature phytase  Multiple cloning site
          peptide
```

Oligonucleotide duplex E

```
5' AATTCAGATCTCCATGGATCGATGAGCT 3'
3'     GTCTAGAGGTACCTAGCTAC     5'
```

FIG. 4B

EXPRESSION OF PHYTASE IN PLANTS

This is a continuation in part of application Ser. No. 756,864 filed Sep. 11, 1991 now abandoned, which is a continuation in part of Ser. No. 586,765 filed Sep. 21, 1990 now abandoned.

BACKGROUND OF THE DISCLOSURE

TECHNICAL FIELD

The present invention pertains to the production of phytase in transgenic plants and the use of the thus-produced phytase in industrial processes.

BACKGROUND OF THE INVENTION

Phosphorus is an essential element for the growth of all organisms. In livestock production, feed must be supplemented with inorganic phosphorus in order to obtain a good growth performance of monogastric animals (e.g. pigs, poultry and fish).

In contrast, no inorganic phosphate needs to be added to the feedstuffs of ruminant animals. Microorganisms, present in the rumen, produce enzymes which catalyze the conversion of phytate (myo-inositolhexakis-phosphate) to inositol and inorganic phosphate.

Phytate occurs as a storage phosphorus source in virtually all feed substances originating from plants (for a review see: *Phytic acid, chemistry and applications*, E. Graf (ed.), Pilatus Press; Minneapolis, Minn., U.S.A. (1986)). Phytate comprises 1–3% of all nuts, cereals, legumes, oil seeds, spores and pollen. Complex salts of phytic acid are termed phytin. Phytic acid is considered to be an anti-nutritional factor since it chelates minerals such as calcium, zinc, magnesium, iron and may also react with proteins, thereby decreasing the bioavailability of proteins and nutritionally important minerals.

Phytate phosphorus passes through the gastro-intestinal tract of monogastric animals and is excreted in the manure. Though some hydrolysis of phytate does occur in the colon, the thus-released inorganic phosphorus has no nutritional value since inorganic phosphorus is absorbed only in the small intestine. As a consequence, a significant amount of the nutritionally important phosphorus is not used by monogastric animals, despite its presence in the feed.

The excretion of phytate phosphorus in manure has further consequences. Intensive livestock production has increased enormously during the past decades. Consequently, the amount of manure produced has increased correspondingly and has caused environmental problems in various parts of the world. This is due, in part, to the accumulation of phosphate from manure in surface waters which has caused eutrophication.

The enzymes produced by microorganisms, which catalyze the conversion of phytate to inositol and inorganic phosphorus are broadly known as phytases. Phytase producing microorganisms comprise bacteria such as *Bacillus subtilis* (V. K. Paver and V. J. Jagannathan (1982) J. Bacteriol. 151, 1102) and *Pseudomonas* (D. J. Cosgrove (1970) Austral. J. Biol. Sci. 23, 1207); yeasts such as *Saccharomyces cerevisiae* (N. R. Nayini and P. Markakis (1984) Lebensmittel Wissenschaft und Technologie 17, 24); and fungi such as *Aspergillus terreus* (K. Yamada, Y. Minoda and S. Yamamoto (1986) Agric. Biol. Chem. 32, 1275). Various other Aspergillus species are known to produce phytase, of which, the phytase produced by *Aspergillus ficuum* has been determined to possess one of the highest levels of specific activity, as well as having better thermostability than phytases produced by other microorganisms (van Gorcom et al. (1991) European Patent Application 89202436.5, Publication No. 0 420 358, filed Sep. 27, 1989).

Phytases are also endogenously present in many plant species (see Loewus, F. A. (1990) In: *Plant Biology* vol. 9: "Inositol metabolism in plants" (eds. D. J. Morré, W. F. Boss, F. A. Loewus) 13). Gellatly, K. S. and Lefebvre, D. D. ((1990) Plant Physiology (supplement), 93, abstract 562) mention the isolation and characterization of a phytase cDNA clone obtained from potato tubers. Gibson, D. M. et al. and Christen, A. A. et al. ((1988) J. Cell Biochem., 12C, abstracts L407 and L402, respectively) mention the synthesis of endogenous phytase during the germination of soybean seeds. However, plant phytases are normally produced in amounts insufficient for their application in industrial processes, per se.

The concept of adding microbial phytase to the feedstuffs of monogastric animals has been previously described (Ware, J. H., Bluff, L. and Shieh, T. R. (1967) U.S. Pat. No. 3,297,548; Nelson, T. S., Shieh, T. R., Wodzinski, R. J. and Ware, J. H. (1971) J. Nutrition 101, 1289). To date, however, application of this concept has not been commercially feasible, due to the high cost of the production of the microbial enzymes (Y. W. Han (1989) Animal Feed Sci. and Technol. 24, 345). For economic reasons, inorganic phosphorus is still added to monogastric animal feedstuffs.

Phytases have found other industrial uses as well. Exemplary of such utilities is an industrial process for the production of starch from cereals such as corn and wheat. Waste products comprising e.g. corn gluten feeds from such a wet milling process are sold as animal feed. During the steeping process phytase may be supplemented. Conditions (T≈50° C. and pH=5.5) are ideal for fungal phytases (see e.g. European Patent Application 0 321 004 to Alko Ltd.). Advantageously, animal feeds derived from the waste products of this process will contain phosphate instead of phytate.

It has also been conceived that phytases may be used in soy processing (see Finase™ Enzymes By Alko, a product information brochure published by Alko Ltd., Rajamäki, Finland). Soybean meal contains high levels of the anti-nutritional factor phytate which renders this protein source unsuitable for application in baby food and feed for fish, calves and other non-ruminants. Enzymatic upgrading of this valuable protein source improves the nutritional and commercial value of this material.

The possibility of using transgenic plants as a production system for valuable proteins has been proposed. Examples to date are the production of interferon in tobacco (Goodman, R. M., Knauf, V. C., Houck, C. M. and Comai, L. (1987) PCT/WO 87/00865), enkephalins in tobacco, *Brassica napus* and *Arabidopsis thaliana* (Vandekerckhove, J., Van Damme, J., Van Lijsebettens, M., Botterman, J., DeBlock, M., DeClerq, A., Leemans, J., Van Montagu, M. and Krebbers, E. (1989) Bio/Technol. 7, 929), antibodies in tobacco (Hiatt, A., Cafferkey, R. and Boedish, K. (1990) Nature 342, 76) and human serum albumin in tobacco and potato (Sijmons, P. C., Dekker, B. M. M., Schrammeijer, B., Verwoerd, T. C., van den Elzen, P. J. M. and Hoekema, A. (1990) Bio/Technol. 8, 217).

In practice, the transformation of an increasing number of plant species, especially dicotyledonous species (e.g. tobacco, potato, tomato, Petunia, Brassica), has become a routine procedure for workers skilled in the art (Klee, H., Horsch, R. and Rogers, S. (1987) Annu. Rev. Plant Physiol. 38, 467; Gasser C. S. and Fraley, R. T. (1989) Science 244, 1293). Strategies for the expression of foreign genes in plants have become well established (Gasser and Fraley, supra). Regulatory sequences from plant genes have been identified that are used for the construction of chimeric genes that can be functionally expressed in plants and plant cells.

For the introduction of gene constructions into plants, several technologies are available, such as transformation with *Agrobacterium tumefaciens* or *Agrobacterium rhizogenes*. Using this strategy, a wide variety of plant tissues have been exploited, the choice being largely dependent on the plant species and its amenability in tissue culture. Successful examples are the transformation of protoplasts, microspores or pollen, and explants such as leaves, stems, roots, hypocotyls and cotyls. Furthermore, methods for direct DNA introduction in protoplasts and plant cells or tissues are used such as microinjection, electroporation, particle bombardment and direct DNA uptake (Gasser and Fraley, supra).

Proteins may be produced in plants using a variety of expression systems. For instance, the use of a constitutive promoter such as the 35S promoter of Cauliflower Mosaic Virus (CaMV) (Guilley, H., Dudley, R. K., Jonard, G., Balazs, E. and Richards, K. E. (1982) Cell 30, 763) will result in the accumulation of the expressed protein in all organs of the transgenic plant. Alternatively, use may be made of promoters from genes encoding proteins which are expressed in a highly tissue-specific and stage-specific manner (Higgins, T. J. V., (1984) Annu. Rev. Plant Physiol. 35, 191; Shotwell, M. A. and Larkins, B. A. (1989) In: *The biochemistry of plants* Vol. 15 (Academic Press, San Diego: Stumpf, P. K. and Conn, E. E., eds.), 297), i.e., the genes are expressed only in the target tissue and only during the desired stage of development.

It will be appreciated that an economical procedure for the production of phytase will be of significant benefit to, inter alia, the animal feed industry. One method of producing a more economical phytase would be to use recombinant DNA techniques to produce transgenic plants or plant organs capable of expressing phytase which could then in turn be added as such, for example, to animal food or feedstuffs for direct consumption by the animal. Alternatively, the phytase expressed in these transgenic plants or plant organs could be extracted and if desired, purified for the desired application.

SUMMARY OF THE INVENTION

Disclosure of the Invention

The present invention provides for the expression of phytase in transgenic plants or plant organs and methods for the production of such plants. This is achieved via the introduction into the plant of an expression construct comprising a DNA sequence encoding a protein having phytase activity.

The DNA expression constructs provided by the present invention for the transformation of plants are under the control of regulatory sequences which are capable of directing the expression of phytase. These regulatory sequences may also include sequences capable of directing transcription in plants, either constitutively, or stage and/or tissue specific, depending on the use of the plant or parts thereof.

The transgenic plants and plant organs provided by the present invention may be applied to a variety of industrial processes either directly, e.g. in animal food or feedstuffs or alternatively, the expressed phytase may be extracted and if desired, purified before application.

DESCRIPTION OF PREFERRED EMBODIMENTS

Brief Description of the Drawings

FIG. 2 (SEQ ID NO: 19 and SEQ ID NO:20 ) shows the nucleotide sequence of the translated region of the phytase cDNA fragment and the derived amino acid sequence of the phytase protein; the start of the mature phytase protein is indicated as position +1.

FIG. 4 (SEQ ID NO:22 through SEQ ID NO:31) shows the sequences of oligonucleotide duplexes used in cloning.

DETAILED DESCRIPTION OF THE INVENTION

Figure 1:
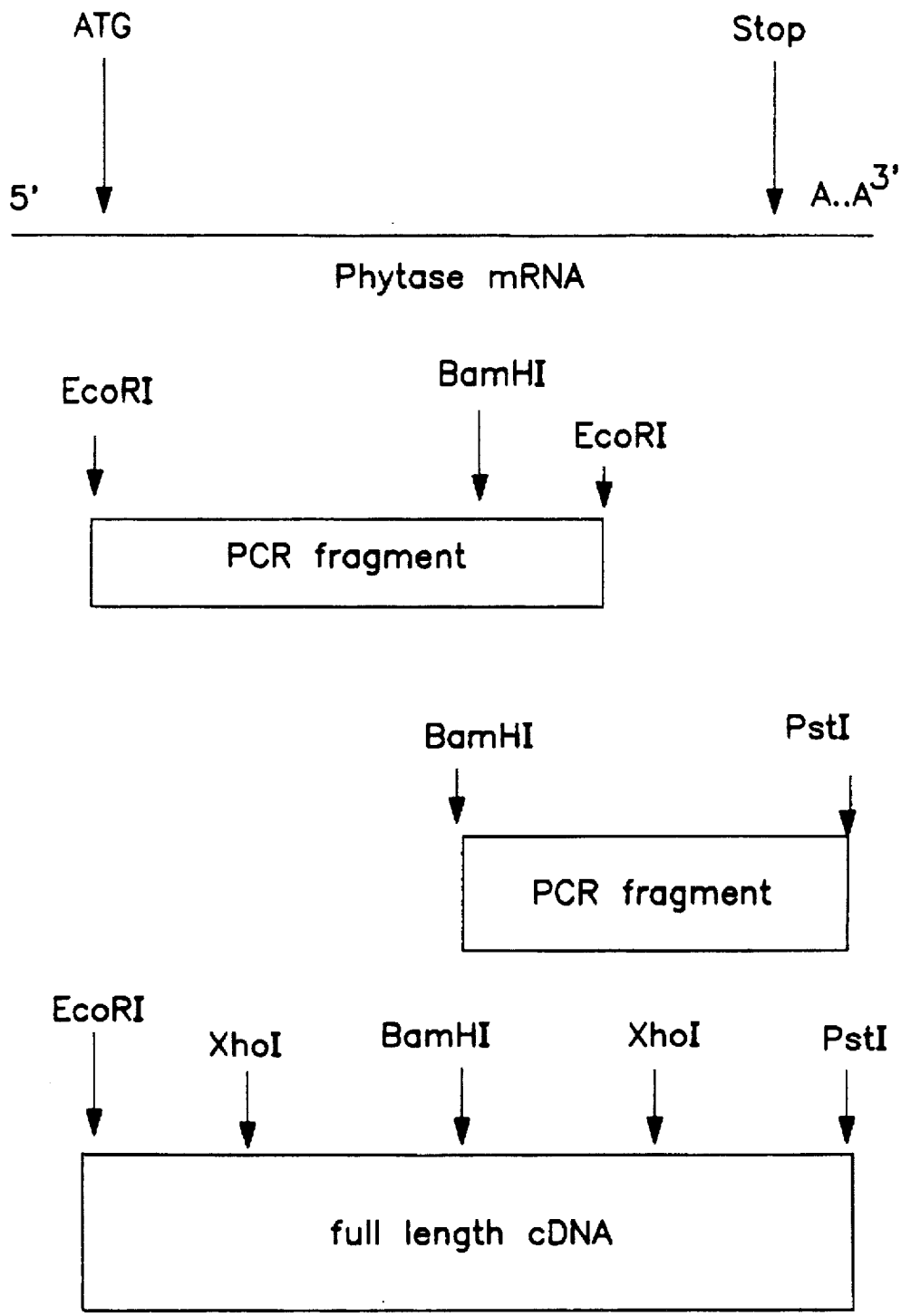
FIG. 1 is a schematic showing the strategy for cloning phytase cDNA.
Figure 3:
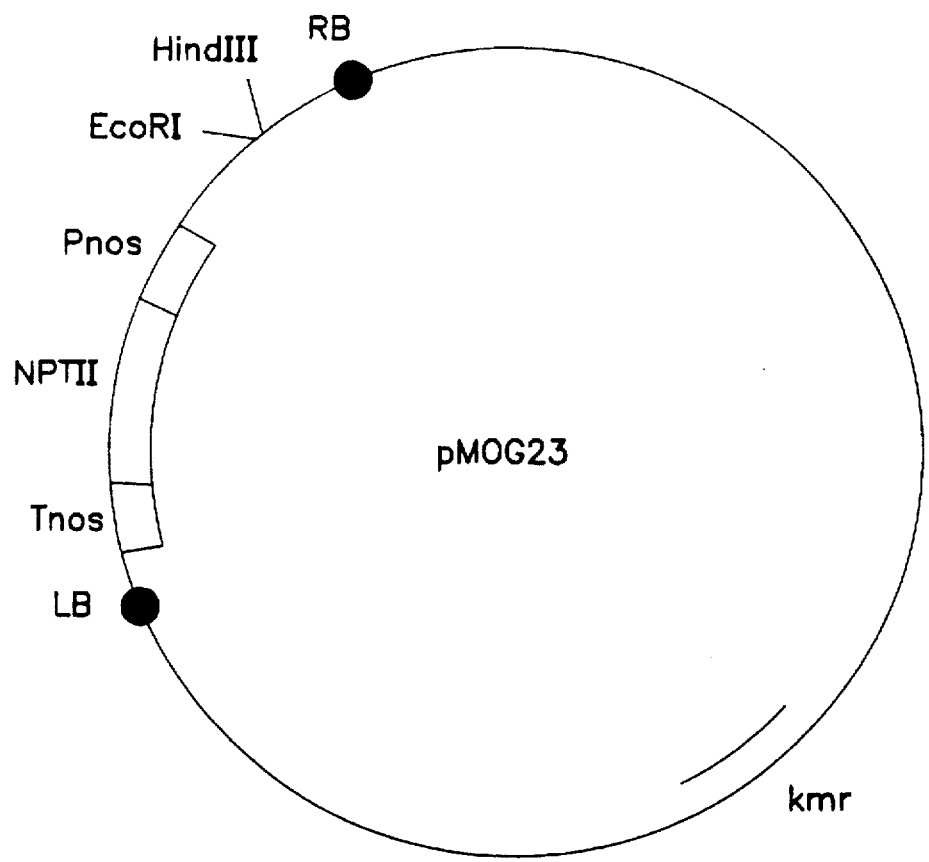
FIG. 3 (SEQ ID NO:21) is a diagram of binary vector pMOG23.

According to the present invention, transgenic plants or plant organs are obtained in which phytase is produced. This is achieved via the introduction into the plant of an expression construct comprising a DNA sequence encoding a protein having phytase activity.

DNA expression constructs are provided by the present invention for the stable transformation of plants with a gene encoding a phytase. These constructs comprise a DNA sequence encoding a phytase which is operably linked to regulatory sequences which are capable of directing the expression of phytase. These regulatory sequences may also include sequences capable of directing transcription in plants, either constitutively, or stage and/or tissue specific, depending on the use of the plant or parts thereof.

The expression constructs provided by the present invention may be inserted into a vector, preferably a plasmid, used in bacteria-mediated transformation of the selected plant host. The expression construct is then preferably integrated into the genome of the plant host.

Within the context of the present invention, the term phytase embraces a family of enzymes which catalyze reactions involving the liberation of inorganic phosphorus from various myoinositol phosphates. This is understood to embrace all proteins having phytase activity.

The DNA sequence encoding phytase may be obtained from a variety of sources such as microbial, plant or animal sources. Preferably, the DNA sequence is obtained from a microbial source such as the filamentous fungus Aspergillus. Most preferred DNA sequences are obtained from *Aspergillus ficuum, Aspergillus niger, Aspergillus awamori* and *Aspergillus nidulans*.

The cloning of a gene or a cDNA encoding a phytase protein may be achieved using various methods. One method is by purification of the phytase protein, subsequent determination of the N-terminal and several internal amino acid sequences and screening of a genomic or cDNA library of the organism producing the phytase, using oligonucleotide probes based on the amino acid sequences.

If at least a partial sequence of the gene is known, this information may be used to clone the corresponding cDNA using, for instance, the polymerase chain reaction (PCR) (PCR Technology: *Principles and Applications for DNA Amplification*, (1989) H. A. Ehrlich, ed., Stockton Press, New York).

It will be evident to those skilled in the art that the cloned phytase gene described above may be used in heterologous hybridization experiments, directed to the isolation of phytase encoding genes from other micro-organisms.

In another aspect, the cloned phytase gene described above may be used as starting materials for the construction of "second generation" phytases. "Second generation" phytases are phytases, altered by mutagenesis techniques (e.g. site-directed mutagenesis), which have properties that differ from those of wild-type phytases or recombinant phytases such as those produced by the present invention. For example, the temperature or pH optimum, specific activity or substrate affinity may be altered so as to be better suited for application in a defined process.

The isolation of the cDNA encoding phytase enables the construction of expression constructs capable of directing the production of phytase in the selected plant host via the application of recombinant DNA techniques such as the exchange of regulatory elements such as e.g. promoters, secretional signals, or combinations thereof.

Phytase may be produced constitutively in the transgenic plants during all stages of development. Depending on the use of the plant or plant organs, the enzymes may be expressed in a stage-specific manner, for instance during tuber formation or fruit development. Also, depending on the use, the enzymes may be expressed tissue-specifically, for instance in plant organs such as fruit, tubers, leaves or seeds.

Transgenic plants, as defined in the context of the present invention include plants (as well as parts and cells of said plants) and their progeny, which have been genetically modified using recombinant DNA techniques to cause or enhance production of a phytase in the desired plant or plant organ.

In the context of the present invention, the phrase "an enhanced amount of phytase" refers specifically to a statistically significant amount of plant tissue which, on average, contain a statistically significant greater amount of phytase as compared with the average amount of phytase enzyme found in an equal amount of non-modified plant tissue.

Within the context of the present invention, plants to be selected include, but are not limited to crops producing edible flowers such as cauliflower (*Brassica oleracea*), artichoke (*Cynara scolymus*), fruits such as apple (Malus, e.g. *domesticus*), banana (Musa, e.g. *acuminata*), berries (such as the currant, Ribes, e.g. *rubrum*), cherries (such as the sweet cherry, Prunus, e.g. *avium*), cucumber (Cucumis, e.g. *sativus*), grape (Vitis, e.g. *vinifera*), lemon (*Citrus limon*), melon (*Cucumis melo*), nuts (such as the walnut, Juglans, e.g. *regia*; peanut, Arachis hypogeae), orange (Citrus, e.g. *maxima*), peach (Prunus, e.g. *persica*), pear (Pyra, e.g. *communis*), plum (Prunus, e.g. *domestica*), strawberry (Fragaria, e.g. *moschata*), tomato (Lycopersicon, e.g. *esculentum*), leafs, such as alfalfa (Medicago, e.g. *sativa*), cabbages (e.g. *Brassica oleracea*), endive (Cichoreum, e.g. *endivia*), leek (Allium, e.g. *porrum*), lettuce (Lactuca, e.g. *sativa*), spinach (Spinacia e.g. *oleraceae*), tobacco (Nicotiana, e.g. *tabacum*), roots, such as arrowroot (Maranta, e.g. *arundinacea*), beet (Beta, e.g. *vulgaris*), carrot (Daucus, e.g. *carota*), cassava (Manihot, e.g. *esculenta*), turnip (Brassica, e.g. *rapa*), radish (Raphanus, e.g. *sativus*), yam (Dioscorea, e.g. *esculenta*), sweet potato (*Ipomoea batatas*) and seeds, such as bean (Phaseolus, e.g. *vulgaris*), pea (Pisum, e.g. *sativum*), soybean (Glycin, e.g. *max*), wheat (Triticum, e.g. *aestivum*), barley (Hordeum, e.g. *vulgare*), corn (Zea, e.g. *mays*), rice (Oryza, e.g. *sativa*), rapeseed (Brassica napus), millet (Panicum L.), sunflower (*Helianthus annus*), oats (*Avena sativa*), tubers, such as kohlrabi (Brassica, e.g. *oleraceae*), potato (Solanum, e.g. *tuberosum*) and the like.

The choice of the plant species is primarily determined by the intended use of the plant or parts thereof and the amenability of the plant species to transformation. Several techniques are available for the introduction of the expression construct containing the phytase-encoding DNA sequence into the target plants. Such techniques include but are not limited to transformation of protoplasts using the calcium/polyethylene glycol method, electroporation and microinjection or (coated) particle bombardment (Potrykus, I. (1990) Bio/Technol. 8, 535).

In addition to these so-called direct DNA transformation methods, transformation systems involving vectors are widely available, such as viral vectors (e.g. from the Cauliflower Mosaic Virus (CaMV) and bacterial vectors (e.g. from the genus Agrobacterium) (Potrykus, supra). After selection and/or screening, the protoplasts, cells or plant parts that have been transformed can be regenerated into whole plants, using methods known in the art (Horsch, R. B., Fry, J. E., Hoffmann, N. L., Eichholtz, D., Rogers, S. G. & Fraley, R. T. (1985) Science 227, 1229). The choice of the transformation and/or regeneration techniques is not critical for this invention.

For dicots, a preferred embodiment of the present invention uses the principle of the binary vector system (Hoekema, A., Hirsch, P. R., Hooykaas, P. J. J. and Schilperoort, R. A. (1983) Nature 303, 179; Schilperoort, R. A., Hoekema, A. and Hooykaas, P. J. J. (1984) European Patent Application No. 0 120 516) in which Agrobacterium strains are used which contain a vir plasmid with the virulence genes and a compatible plasmid containing the gene construct to be transferred. This vector can replicate in both *E. coli* and in Agrobacterium, and is derived from the binary vector Bin19 (Bevan, M. (1984) Nucl. Acids Res. 12, 8711) which is altered in details that are not relevant for this invention. The binary vectors as used in this example contain between the left- and right-border sequences of the T-DNA, an identical NPTII-gene coding for kanamycin resistance (Bevan, supra) and a multiple cloning site to clone in the required gene constructs.

The transformation and regeneration of monocotyledonous crops is not a standard procedure. However, recent scientific progress shows that in principle monocots are amenable to transformation and that fertile transgenic plants can be regenerated from transformed cells. The development of reproducible tissue culture systems for these crops, together with the powerful methods for introduction of genetic material into plant cells has facilitated transformation. Presently the methods of choice for transformation of monocots are microprojectile bombardment of explants or suspension cells, and direct DNA uptake or electroporation of protoplasts. For example, transgenic rice plants have been successfully obtained using the bacterial hph gene, encoding hygromycin resistance, as a selection marker. The gene was introduced by electroporation (Shimamoto, K., Terada, R., Izawa, T. and Fujimoto, H. (1989) Nature 338, 274). Transgenic maize plants have been obtained by introducing the *Streptomyces hygroscopicus* bar gene, which encodes phosphinothricin acetyltransferase (an enzyme which inactivates the herbicide phosphinothricin), into embryogenic cells of a maize suspension culture by microparticle bombardment (Gordon-Kamm, W. J., Spencer, T. M., Mangano, M. L., Adams, T. R., Daines, R. J., Start, W. G., O'Brien, J. V., Chambers, S. A., Adams Jr., W. R., Willets, N. G., Rice, T. B., Mackey, C. J., Krueger, R. W., Kausch, A. P. and Lemaux, P. G. (1990) The Plant Cell 2, 603). The introduction of genetic material into aleurone protoplasts of other monocot crops such as wheat and barley has been reported (Lee, B., Murdoch, K., Topping, J., Kreis, M. and Jones, M. G. K. (1989) Plant Mol. Biol. 13, 21). Wheat plants have been regenerated from embryogenic suspension culture by selecting only the aged compact and nodular embryogenic callus tissues for the establishment of the embryogenic suspension cultures (Vasil, V., Redway, F. and Vasil, I. K. (1990) Bio/Technol. 8, 429). The combination with transformation systems for these crops enables the application of the present invention to monocots. These methods may also be applied for the transformation and regeneration of dicots.

Expression of the phytase construct involves such details as transcription of the gene by plant polymerases, translation of mRNA, etc. that are known to persons skilled in the art of recombinant DNA techniques. Only details relevant for the proper understanding of this invention are discussed below.

Regulatory sequences which are known or are found to cause expression of phytase may be used in the present invention. The choice of the regulatory sequences used depends on the target crop and/or target organ of interest. Such regulatory sequences may be obtained from plants or plant viruses, or may be chemically synthesized. Such regulatory sequences are promoters active in directing transcription in plants, either constitutively or stage and/or tissue specific, depending on the use of the plant or parts thereof. These promoters include, but are not limited to promoters showing constitutive expression, such as the 35S promoter of Cauliflower Mosaic Virus (CaMV) (Guilley et al. (1982) Cell 30, 763), those for leaf-specific expression, such as the promoter of the ribulose bisphosphate carboxylase small subunit gene (Coruzzi et al., (1984) EMBO J., 3, 1671), those for root-specific expression, such as the promoter from the glutamine synthase gene (Tingey et al. (1987) EMBO J., 6, 3565), those for seed-specific expression, such as the cruciferin A promoter from *Brassica napus* (Ryan et al. (1989) Nucl. Acids Res. 17, 3584), those for tuber-specific expression, such as the class-I patatin promoter from potato (Rocha-Sosa et al, (1989) EMBO J. 8, 23; Wenzler et al, (1989) Plant Mol. Biol. 12, 41) or those for fruit-specific expression, such as the polygalacturonase (PG) promoter from tomato (Bird et al, (1988) Plant Mol. Biol. 11, 651).

Other regulatory sequences such as terminator sequences and polyadenylation signals include any such sequence functioning as such in plants, the choice of which is within the level of the skilled artisan. An example of such sequences is the 3' flanking region of the nopaline synthase (nos) gene of *Agrobacterium tumefaciens* (Bevan, M., supra).

The regulatory sequences may also include enhancer sequences, such as found in the 35S promoter of CaMV, and mRNA stabilizing sequences such as the leader sequence of Alfalfa Mosaic Virus (AlMV) RNA4 (Brederode, F. T., Koper-Zwarthoff, E. C. & Bol, J. F. (1980) Nucl. Acids Res. 8, 2213) or any other sequences functioning in a like manner.

The phytase should be expressed in an environment that allows for stability of the expressed protein. The choice of cellular compartments, such as cytosol, endoplasmic reticulum, vacuole, protein body or periplasmic space can be used in the present invention to create such a stable environment, depending on the biophysical parameters of the phytase. Such parameters include, but are not limited to pH-optimum, sensitivity to proteases or sensitivity to the molarity of the preferred compartment.

To obtain expression in the cytoplasm of the cell, the expressed enzyme should not contain a secretory signal peptide or any other target sequence. For expression in chloroplasts and mitochondria the expressed enzyme should contain a specific so-called transit peptide for import into these organelles. Targeting sequences that can be attached to the enzyme of interest in order to achieve this are known (Smeekens et al, (1990) T.I.B.S. 15, p.73; van den Broeck et al., (1985) Nature 313, 358; Schreier et al., (1985) EMBO J. 4, 25). If the activity of the enzyme is desired in the vacuoles a secretory signal peptide has to be present, as well as a specific targeting sequence that directs the enzyme to these vacuoles (Tague et al, (1988) Plant Phys. 86, 506). The same is true for the protein bodies in seeds. The DNA sequence encoding the enzyme of interest should be modified in such a way that the enzyme can exert its action at the desired location in the cell.

To achieve extracellular expression of the phytase, the expression construct of the present invention utilizes a secretory signal sequence. Although signal sequences which are homologous (native) to the plant host species are preferred, heterologous signal sequences, i.e. those originating from other plant species or of microbial origin, may be used as well. Such signal sequences are known to those skilled in the art. Appropriate signal sequences which may be used within the context of the present invention are disclosed in Walter, P. and Blobel, G. (1986) Biochem. Soc. Symp., 47, 183; Von Heijne, G. (1986) J. Mol. Biol., 189, 239; and Sijmons, P. C., Dekker, B. M. M., Schrammeijer, B., Verwoerd, T. C., van den Elzen, P. J. M. and Hoekema, A. (1990) Bio/Technol., 8, 217.

All parts of the relevant DNA constructs (promoters, regulatory-, secretory-, stabilizing-, targeting- or termination sequences) of the present invention may be modified, if desired, to affect their control characteristics using methods known to those skilled in the art.

It is pointed out that plants containing phytase obtained via the present invention may be used to obtain plants or plant organs with yet higher phytase levels. For example, it may be possible to obtain such plants or plant organs by the use of somoclonal variation techniques or by cross breeding techniques. Such techniques are well known to those skilled in the art.

In one embodiment of the present invention, a double-stranded cDNA encoding phytase is prepared from mRNA isolated from *Aspergillus ficuum*. The DNA construct is placed under the control of regulatory sequences from the gene encoding the 12S storage protein cruciferin from *Brassica napus*. The construct is thereafter subcloned into a binary vector such as pMOG23 (in *E. coli* K-12 strain DH5α, deposited at the Centraal Bureau voor Schimmelcultures, Baarn, The Netherlands on Jan. 29, 1990 under accession number CBS 102.90). This vector is introduced into *Agrobacterium* tumefaciens which contains a disarmed Ti plasmid. Bacterial cells containing this construct are co-cultivated with tissues from tobacco or Brassica plants, and transformed plant cells are selected by nutrient media containing antibiotics and induced to regenerate into differentiated plants on such media. The resulting plants will produce seeds that contain and express the DNA construct.

In another embodiment of the present invention, the phytase-encoding DNA construct is placed under the control of regulatory sequences from the 35S promoter of Cauliflower Mosaic Virus (CaMV). The construct is thereafter subcloned into a binary vector. This vector is then introduced into *Agrobacterium tumefaciens* which contains a disarmed Ti plasmid. Bacterial cells containing this construct are co-cultivated with tissues from tobacco or Brassica plants, and transformed plant cells are selected by nutrient media containing antibiotics and induced to regenerate into differentiated plants on such media. The resulting plants contain and express the DNA construct constitutively.

Phytase activity may be measured via a number of assays, the choice of which is not critical to the present invention. For example, the phytase enzyme activity of the transgenic plant tissue may be tested with an ELISA-assay, Western blotting or direct enzyme assays using colorimetric techniques or native gel assays.

The plant or plant organ containing phytase, as produced via the present invention may be used in a variety of industrial processes requiring the action of a phytase.

The plants or plant organs containing phytase produced according to the present invention may be used in industrial processes requiring the action of a phytase. Examples of such applications are in feed additives for non-ruminants, in soy processing, or in the production of inositol or inositol-phosphates from phytate. Other industrial processes using substrates that contain phytate such as the starch industry and in fermentation industries, such as the brewing industry. Chelation of metal ions by phytate may cause these minerals to be unavailable for the production microorganisms. Enzymatic hydrolysis of phytate prevents these problems.

Phytase produced in plants can also be used in a process for steeping corn or sorghum kernels. The plant tissue may be ground before adding to steeping corn. Phytase liberated from the plant tissue can act on phytin, which is present in many corn preparations. Degradation of phytin in steeping corn is beneficial for the added commercial value of corn steep liquor, which is used as animal feed or as a nutrient in microbial fermentations. Furthermore, the degradation of phytin can prevent problems relating to the accumulation of deposits in filters, pipes, reactor vessels, etc. during concentration, transport and storage of corn steep liquor (Vaara, T. et al. (1989) European Patent Application 0 321 004). The action of phytase can also accelerate the steeping process and the separation processes involved in corn wet milling.

The plants or plant organs may be used directly, i.e. without further processing, or may first be processed via conventional means such as grinding to the desired consistency before application.

Alternatively, the phytase may be extracted from the plant or plant organ and, if desired, purified before use using conventional extraction methods and purification techniques.

The production of phytases in plants which are compatible with the intended application provides convenience and will reduce production costs as compared to that of microbial phytases in order to allow its economical application, e.g. in animal feed, which eventually will lead to a price/in vivo performance ratio competitive with inorganic phosphate. As a further benefit, the phosphorus content of manure will be considerably decreased.

It will be appreciated that the application of phytases, available at a price competitive with inorganic phosphate, will increase the degrees of freedom for the compound feed industry to produce a high quality feed. For example, when feed is supplemented with phytase, the addition of inorganic phosphate may be omitted and the contents of various materials containing phytate may be increased.

The following examples are provided so as a to give those of ordinary skill in the art a complete disclosure and description of how to make and use the invention and are not intended to limit the scope of what the inventors regard as their invention. Efforts have been made to ensure accuracy with respect to numbers used (e.g., amounts, temperature, pH, etc.) but some experimental errors and deviation should be accounted for. Unless indicated otherwise, temperature is in degrees Centigrade and pressure is at or near atmospheric.

EXAMPLE 1

Isolation of poly A$^+$ RNA from *Aspergillus ficuum*

*A. ficuum* strain NRRL 3135 is grown in a medium containing 22.72 g/l maize flour (amylase treated at pH 7 at 85° C. during 15 minutes), 9.36 g/l glucose, 2.9 g/l $KNO_3$, 0.142 g/l KCl 0.142 g/l $MgSO_4.7H_2O$ and 56.8 mg/l $FeSO_4.7H_2O$. After 6 days the mycelium is harvested.

Dry mycelium (0.5 g) is frozen with liquid nitrogen and ground. Subsequently the material is homogenized with an Ultra turrax (full speed, 1 minute) at 0° C. in 3M LiCl, 6M Urea and maintained overnight at 4° C. as described by Auffray and Rougeon (1980) Eur. J. Biochem. 107, 303. Total cellular RNA is obtained after centrifugation at 16,000× g, which is followed by two successive extractions with phenol:chloroform:isoamylalcohol (50:48:2). The RNA is precipitated with ethanol and redissolved in 1 ml 10 mM Tris-HCl (pH 7.4), 0.5% SDS. For poly A$^+$ selection the total RNA sample is heated for 5 minutes at 65° C., adjusted to 0.5M NaCl and subsequently applied to an oligo(dT)-cellulose column. After several washes with an solution containing 10 mM Tris pH 7.0, 1 mM EDTA and 0.1 mM NaCl the poly A$^+$ RNA is collected by elution with 10 mM Tris pH 7.0 and 1 mM EDTA.

EXAMPLE 2

Preparation and cloning of a cDNA encoding phytase

For the synthesis of the first strand of the cDNA 5 μg of poly A$^+$ RNA, isolated according to Example 1, is dissolved in 16.5 μl $H_2O$ and the following components are added: 2.5 μl RNasin (30 U/μl), 10 μl of a buffer containing 50 mM Tris-HCl pH 7.6, 6 mM $MgCl_2$ and 40 mM KCl, 2 μl 1M KCl, 5 μl 0.1M DTT, 0.5 μl oligo(dT)$_{12-18}$ (2.5 mg/ml), 5 μl 8 mM dNTP-mix, 5μl BSA (1 mg/ml) and 2.5 μl Moloney MLV reverse transcriptase (200 U/μl). The mixture is incubated for 30 minutes at 37° C. and the reaction is stopped by addition of 10 μl 0.2M EDTA and 50 μl $H_2O$. An extraction is performed using 110 μl chloroform and after centrifugation for 5 minutes 5M $NH_4Ac$ and 440 μl absolute ethanol (−20° C.) are added to the supernatant. Precipitation is done in a dry ice/ethanol solution for 30 minutes. After centrifugation (10 minutes at 0° C.) the cDNA/mRNA pellet is washed with 70% ice-cold ethanol. The pellet is dried and dissolved in 20 µl of $H_2O$.

Isolation of the cDNA encoding phytase is performed with the Polymerase Chain Reaction (PCR) in two fragments. The two fragments are combined, using the BamHI site within the gene to create a full length cDNA. The strategy for the cloning of the phytase cDNA is shown in FIG. 1.

Partial sequencing of the phytase gene (Van Gorcom et al., supra), reveals the presence of a BamHI site at approximately 800 basepairs from the initiation codon. The nucleotide sequence around this BamHI site, as well as the nucleotide sequence preceding the start codon and the nucleotide sequence after the stop codon of the phytase gene are used to design oligonucleotides for the PCR.

The polymerase chain reaction is performed according to the supplier of Taq-polymerase (cetus) using 1.5 µl of the solution containing the reaction product of the first strand synthesis and 0.5 µg of each of the oligonucleotides. Amplification is performed in a DNA amplifier of Perkin Elmer/Cetus. After 25 cycles of 2 minutes at 94° C., 2 minutes at 55° C. and 3 minutes at 72° C. the reaction mixture is deproteinized by subsequent phenol and chloroform extractions. The DNA is precipitated, redissolved in a buffer containing 10 mM Tris, pH 7 and 0.1 mM EDTA and subsequently digested with suitable restriction enzymea For the amplification of the fragment encoding the N-terminal part of the protein, the two following oligonucleotides are used:

Oligo 1: 5' GGGTAGAATTCAAAAATGGGCGTCTCT-GCTGTTCTA 3' (SEQ ID NO:1)

Oligo 2: 5' AGTGACGAATTCGTGCTGGTGGAGATG-GTGTCG 3' (SEQ ID NO:2)

The amplified fragment is digested with EcoRI and cloned into the EcoRI site of pTZ18R (purchased from Pharmacia). Restriction site mapping and nucleotide sequencing demonstrate the authenticity of the fragment. The resulting plasmid is named pGB925.

For the amplification of the second fragment, the following two oligonucleotides are used:

Oligo 3: 5' GAGCACCAAGCTGAAGGATCC 3' (SEQ ID NO:3)

Oligo 4: 5' AAACTGCAGGCGTTGAGTGTGATTGTT-TAAAGGG 3' (SEQ ID NO:4)

The amplified fragment is digested with BamHI and PstI and subsequently cloned into pTZ18R, which has been digested with BamHI and PstI. Restriction site mapping and nucleotide sequencing show that the correct fragment is isolated. The resulting plasmid is named pGB926.

In order to isolate a full length cDNA, pGB925 is digested with EcoRI and BamHI and the fragment containing the phytase encoding DNA is isolated. This fragment is cloned into plasmid pGB926, which has been digested with EcoRI and BamHI, resulting in plasmid pGB927. Plasmid pGB927 contains a full length cDNA encoding phytase, with an approximate size of 1.8 kbp. The sequence of the cDNA region encoding the phytase protein and the derived amino acid sequence of the phytase protein are depicted in FIG. 2.

EXAMPLE 3

Construction of the binary vector pMOG23.

In this example the construction of the binary vector pMOG23 (in *E. coli* K-12 strain DH5α, deposited at the Centraal Bureau voor Schimmel-cultures on Jan. 29, 1990 under accession number CBS 102.90) is described.

The binary vector pMOG23 (FIG. 2) is a derivative of vector Bin19 (Bevan, M., supra). To obtain pMOG23, the vector Bin19 is changed in a way not essential for the present invention, using techniques familiar to those skilled in the art of molecular biology.

First, the positions of the left border (LB) and the right border (RB) are switched with reference to the neomycine phosphotransferase gene II (NPTII gene). Secondly, the orientation of the NPTII gene is reversed giving transcription in the direction of LB. Finally, the polylinker of Bin19 is replaced by a polylinker with the following restriction enzyme recognition sites: EcoRI, KpnI, SmaI, BamHI, XbaI, SacI, XhoI, and HindIII.

EXAMPLE 4

Cloning of the phytase cDNA of *Aspergillus ficuum* in an expression construct for constitutive expression in plants The phytase gene from *Aspergillus ficuum* is tailored and cloned in an expression construct for constitutive expression downstream of the Cauliflower Mosaic Virus 35S promoter. The expression construct also contains the coding information for a signal peptide sequence of plant origin.

The phytase cDNA is cloned into the expression construct as present on plasmid pMOG29 (described under a)). Subsequently the entire construct is introduced into the binary vector pMOG23 and transferred to *Agrobacterium tumefaciens* strain LBA4404.

a) Construction of expression vector pMOG29

Figure 5:
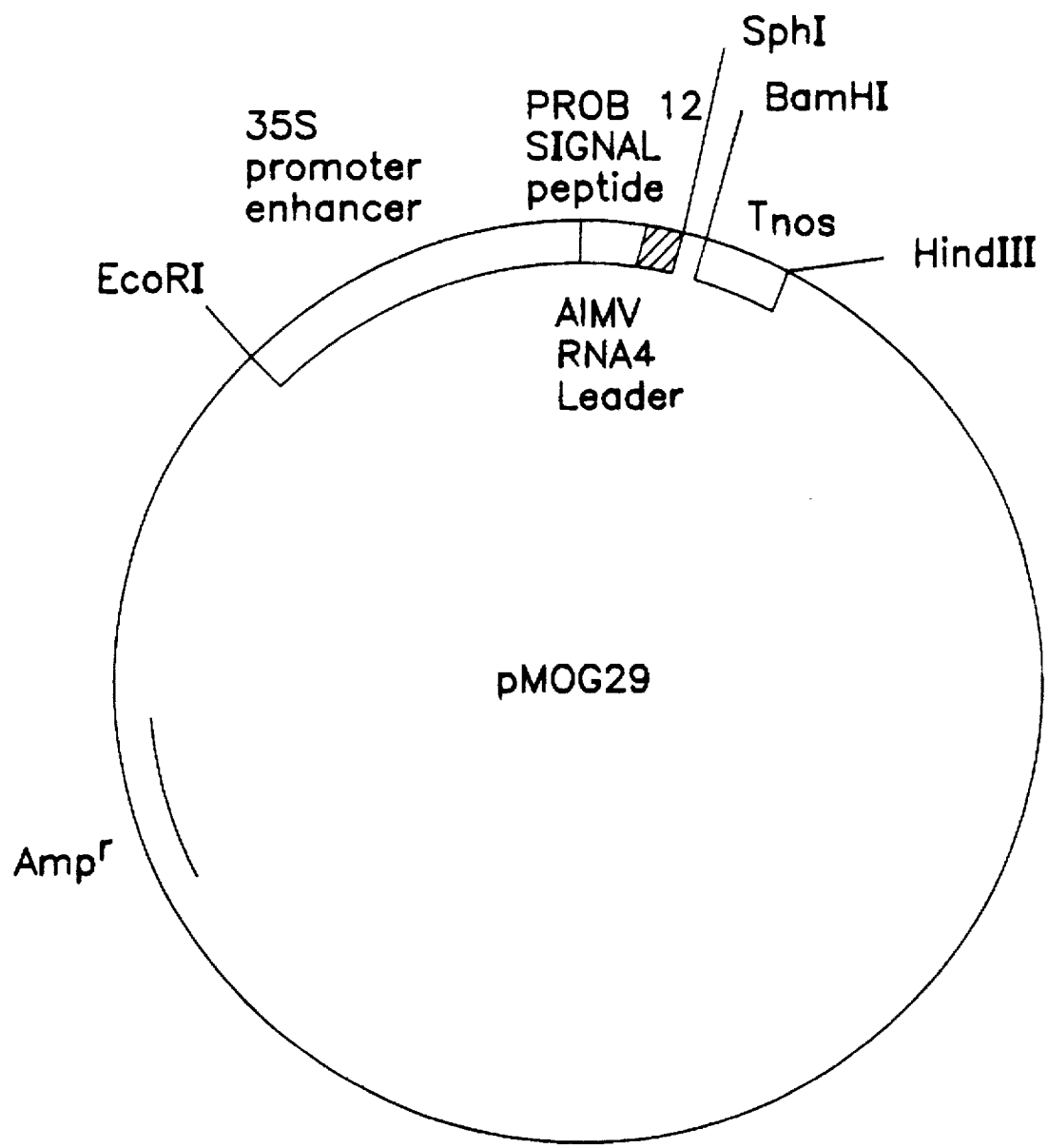
FIG. 5 is a diagram of plasmid pMOG29, Plasmid pUC18 containing an expression cassette for constitutive expression in plants and a sequence encoding a tobacco signal peptide.

The expression construct of ROK1 (Baulcombe et al., (1986) Nature 321, 446) is cloned as an EcoRI/HindIII fragment into pUC18. This construct contains the Cauliflower Mosaic Virus (CaMV) 35S promoter on an EcoRI/BamHI fragment and the nopaline synthase (nos) transcription terminator on a BamHI/HindIII fragment. The promoter fragment consists of the sequence from −800 to +1 of the CaMV 35S promoter. Position +1, which is included, is the transcription initiation site (Guilley et al., supra). The sequence upstream of the NcoI site at position −512 is deleted and this site is changed into an EcoRI site. This is done by cutting the expression construct present in pUC18 with NcoI, filling in the single-stranded ends with Klenow polymerase and ligation of an EcoRI linker. The resulting plasmid is cut with EcoRI, resulting in the deletion of the EcoRI fragment carrying the sequences of the 35S promoter upstream of the original NcoI site. The BamHI/HindIII fragment, containing the nos terminator is replaced by a synthetic DNA fragment (oligonucleotide duplex A, FIG. 4) containing the leader sequence of RNA4 of Alfalfa Mosaic Virus (AlMV) (Brederode et al., supra). This is done by cleavage with BamHI, followed by cleavage with HindIII and ligation of the synthetic DNA fragment. The BamHI site and three upstream nucleotides are deleted by site-directed mutagenesis. In the resulting plasmid, the BamHI/HindIII fragment containing the nos terminator sequence is reintroduced. The gene encoding β-glucuronidase (originating from plasmid pRAJ 275; Jefferson, R. A. (1987) Plant Mol. Biol. Reporter 5, 387) was ligated in as an NcoI/BamHI fragment, resulting in plasmid pMOG14. From the literature it is known that duplication of the sequence between −343 and −90 increases the activity of the 35S promoter (Kay, R., Chan, A., Dayly, M. & McPherson, J. (1987) Science 236, 1299). To obtain a promoter fragment with a double, so-called enhancer sequence, the following steps, known to those skilled in the art, are carried out. From plasmid pMOG14, the enhancer fragment is isolated on an AccI/ EcoRI fragment and subsequently blunt-ended with Klenow polymerase. The obtained fragment is introduced in pMOG14 cut with EcoRI and blunt-ended, in such a way that the border between the blunt-ended EcoRI and AccI sites generate a new EcoRI site. The resulting plasmid (pMOG18) contains the 35S promoter with a double enhancer sequence, the leader sequence of RNA4 from AlMV and the nos terminator in an expression construct still present on an EcoRI/HindIII fragment. Finally, the NcoI/ BamHI fragment encoding β-glucuronidase is replaced with the synthetic DNA fragment B (FIG. 4), derived from the PROB12 cDNA (Cornelissen, B. J. C., Hooft van Huijsduijnen, R. A. M. & Bol, J. F. (1986) Nature 321, 531). This fragment B encodes the PR-protein PR-S signal peptide sequence from tobacco Samsun NN. An SphI site is created in the signal peptide encoding DNA sequence by changing one nucleotide. This change does not alter the amino acid sequence of the encoded PR-S signal peptide. The resulting plasmid is called pMOG29 (FIG. 5).

b) Cloning of the phytase gene from *Aspergillus ficuum* in the binary vector

Oligonucleotide duplex C (FIG. 4) is cloned into plasmid pMOG29, digested with SphI and BamHI, resulting in plasmid pMOG407. The oligonucleotide duplex contains the coding information for the final 2 amino acids of the signal peptide of PR-S, followed by the first 6 amino acids of mature phytase.

The plasmid pGB927, which contains the full length phytase cDNA, is digested with XhoI (partially) and PstI. The XhoI/PstI fragment comprising the DNA sequences encoding mature phytase from amino acid 6 onward is cloned into plasmid pMOG407 linearized with XhoI and PstI, resulting in plasmid pMOG417. The entire construct, containing the chimaeric phytase gene, is inserted as an EcoRI/HindIII fragment into the binary vector pMOG23 linearized with EcoRI and HindIII. The resulting binary plasmid pMOG413 is mobilized, in a triparental mating with the *E. coli* K-12 strain RK2013 (containing plasmid pRK2013) (Ditta, G., Stanfield, S., Corbin, D. & Helinski, D. R. (1980) Proc. Natl. Acad. Sci. USA 77, 7347), into *Agrobacterium tumefaciens* strain LBA4404 that contains a plasmid with the virulence genes necessary for T-DNA transfer to the plant.

EXAMPLE 5

Transient expression of chimaeric phytase gene in tobacco protoplasts

Protoplasts of tobacco are transformed with plasmid DNA carrying the chimaeric phytase gene under regulation of the constitutive CaMV 35S promoter. After 72 hours treated protoplasts are assayed for transient expression of the introduced phytase gene using the phytase activity assay.

Protoplasts are prepared from axenically grown 1-2 months old tobacco plants (*Nicotiana tabacum* SR1). The entire procedure is described by Rodenburg, K. W., DeGroot, M. J. A., Schilperoort, R. A. & Hooykaas, P. J. J. ((1989) Plant Mol. Biol. 13,711). For transformation a number of 5×10⁵ protoplasts is electroporated with 40 μg DNA of plasmid pMOG417). After electroporation protoplasts are resuspended in 3 ml of K3G medium. For the phytase activity assay protoplasts are pelleted and the 3 ml of supernatant is dialyzed overnight against an excess of water. The dialysate is freeze-dried and resuspended in 300 μl 25 mM sodium-acetate pH 5.5. The assay is then carried out as described in detail in Example 10, with the only exception that instead of the 250 mM Glycine HCl buffer pH 2.5, a 25 mM sodium acetate buffer pH 5.5 is used.

In these experiments, one phytase unit (PTU) is defined as 1 μmol of phosphate released from 1.5 mM sodium phytate solution per minute at 37° C. at pH 5.5.

In untreated protoplasts no detectable activity is found. Protoplasts electroporated with plasmid pMOG417 show an activity of 0.26 PTU per mg protein in the supernatant.

EXAMPLE 6

Stable expression of a chimaeric phytase gene in tobacco plants under the control of the CaMV 35S promoter Tobacco is transformed by cocultivation of plant tissue with *Agrobacterium tumefaciens* strain LBA4404 containing the binary vector pMOG413 with the chimaeric phytase gene under regulation of the CaMV 35S promoter. Transformation is carried out using cocultivation of tobacco (*Nicotiana tabacum* SR1) leaf discs according to Horsch et al., supra. Transgenic plants are regenerated from shoots that grow on selection medium (100 mg/l) kanamycin), rooted and transferred to soil. Young plants are assayed for NPTII-activity (kanamycin resistance), grown to maturity and allowed to self-pollenate and set seed.

For phytase activity assays of the leaves of the transgenic plants, a segment of approx. 5 mm in diameter from a young leaf is taken from each plant, and homogenized in 300 μl 25 mM sodium-acetate buffer pH 5.5. Subsequently, phytase assays were carried out as described for the transient assays. In 32 independently transformed tobacco plants tested, a maximum activity was observed of 2 PTU/mg total soluble protein in the extracts. This corresponds to 1.7% of total soluble protein. In the seeds of these transformed tobacco plants, a maximum phytase expression level of 0.4% of the total soluble seed protein was observed. No phytase activity could be detected in untransformed plants.

Two transgenic plant lines, 413.25 and 413.32, were selected on the basis of their high expression levels of phytase.

EXAMPLE 7

Cloning of the phytase cDNA of *Aspergillus ficuum* in a seed-specific expression construct An expression construct is constructed in such a way that seed-specific expression is obtained, using sequences of the *Brassica napus* 12S storage protein gene cruciferin (cruA; Ryan et al., supra). These sequences may be replaced by those from similar seed-specific genes to achieve the same goal as is the objective of this invention.

The phytase cDNA is cloned into the expression construct. Finally, the entire construct is introduced into *Agrobacterium tumefaciens*, which is used for transformation. For all *E. coli* transformations in this example, *E. coli* K-12 strain DH5α is used.

a) Construction of the expression construct

For the construction of the expression construct for seed-specific expression, the promoter and terminator sequences from the cruciferin A (cruA) gene of *Brassica napus* cv. Jet Neuf are synthesized using PCR technology with isolated genomic DNA (Mettler, I. J. (1987) Plant Mol. Biol. Rep. 5, 346) as a template. This gene shows seed-specific expression and its coding and flanking sequences have been determined (Ryan et al., supra).

Two sets of oligonucleotides are synthesized. One to allow amplification of the cruA 5' flanking region and part of the signal peptide encoding sequence as an EcoRI/NcoI fragment:

5' GTTCGGAATTCGGGTTCCGG 3' (SEQ ID NO:5) and 5' AACTGTTGAGCTGTAGAGCC 3' (SEQ ID NO:6). The other for amplification of the 3' flanking sequence as a BglII/HindIII fragment:

5' CTTAAGATCTTACCCAGTGA 3' (SEQ ID NO:7) and 5' CGGAGAAGCTTGCATCTCGT 3' (SEQ ID NO:8).

The oligo's are designed to contain suitable restriction sites at their termini to allow direct assembly of the expression construct after digestion of the fragments with the restriction enzymes.

The 5' fragment of the cruA gene, that includes 54 nucleotides of the sequence encoding the signal peptide is cloned into vector pMOG445 (Oligonucleotide duplex E (FIG. 4) cloned into vector pUC18, linearized with SstI and EcoRI), cut with EcoRI and NcoI, resulting in vector pMOG424. The synthetic oligonucleotide duplex D (FIG. 4), comprising the final 5 coding triplets for the signal sequence of *Brassica napus* cruciferin, the sequence encoding amino acids 1–6 of mature phytase and a multiple cloning site, is cloned in vector pMOG424 cut with NcoI and HindIII. The resulting vector is called pMOG425. The 3' cruA PCR fragment is cloned as a BglII/HindIII fragment into pMOG425 digested with BglII and HindIII, resulting in pMOG426.

b) Cloning of the phytase gene from *Aspergillus ficuum* in the binary vector

Plasmid pGB927, which contains the full-length coding sequence for *Aspergillus ficuum* phytase, is digested with XhoI (partially) and with PstI. The XhoI/PstI fragment comprising the DNA sequences encoding mature phytase from amino acid 6 onward is cloned in vector pMOG426, cut with XhoI and PstI. From the resulting vector pMOG428, the entire construct, containing the chimeric phytase gene, is inserted as an EcoRI/HindIII fragment in the binary vector pMOG23 linearized with EcoRI and HindIII. The resulting binary vector pMOG429 is mobilized, in a triparental mating with the *E. coli* K-12 strain RK2013 (containing plasmid pRK2013) (Ditta et al., supra), into Agrobacterium strain LBA4404 (Hoekema et al., 1983, supra) that contains a plasmid with the virulence genes necessary for T-DNA transfer to the plant.

EXAMPLE 8

Stable seed-specific expression of phytase in tobacco seeds under the control of a cruciferin promoter Agrobacterium strain LBA4404, containing the binary vector pMOG429 with the phytase cDNA under the control of the cruciferin promoter, is used for transformation experiments. Transformation of tobacco (*Nicotiana tabacum* SR1) is carried out using cocultivation of leaf discs according to the procedure of Horsch et al., supra. Transgenic plants are regenerated from shoots that grow on selection medium (100 mg/l kanamycin). Young plants are assayed for NPTII-activity (kanamycin resistance), grown to maturity and allowed to self-pollenate and set seed. Seeds from individual transformants are pooled and part of the seed sample is assayed for the presence of phytase. From clones with the highest expression levels, compared to untransformed control seeds, the remaining seeds are germinated on kanamycin (200 mg/L). From data on the resulting S2 seeds, seeds homozygous for NPTII (hence also for phytase) are selected and used for mass propagation of plants capable of producing the highest amounts of phytase. These can then be used, e.g. for digestion experiments.

To determine the phytase activity found in the transgenic seeds, about 50 mg seed is taken and homogenized with a pestle in an ice-cold mortar in 1 ml 25 mM sodium-acetate buffer pH 5.5. After centrifugation, the supernatant is assayed as described for the transient assays. In 55 independently transformed tobacco plants, a maximum phytase expression level of 0.15% of the total soluble seed protein was observed. Phytase activity was not detected in stems, roots and leaves of the transgenic plants. No phytase activity could be detected in untransformed plants.

EXAMPLE 9

Transformation of rapeseed

In this example, the transformation of rapeseed by co-cultivation of plant tissue with *Agrobacterium tumefaciens*, containing a binary vector with the chimeric phytase gene is described. Transgenic plants may be selected on antibiotic resistance. The transgenic plants may be assayed for phytase activity. High expressors may be analyzed more thoroughly and used in further experiments.

The same chimeric phytase construct in a binary vector (pMOG429) is mobilized into *Agrobacterium tumefaciens* strain LBA4404, in a like manner as described in Example 7. This strain may be used to transform rapeseed (*Brassica napus* cv. Westar). To this aim, surface-sterilized stem segments taken from 5 to 6 week-old plants, just before flowering, are preconditioned for 24 h on MS medium (Fry et al. (1987) Plant Cell Reports 6, 321) with 1 mg/l BAP and then co-cultivated for 48 h with Agrobacterium on fresh plates with the same medium. Transgenic plantlets were regenerated from shoots that grow on selection medium (500 mg/l carbenicilline, 40 mg/l paromomycin) and further analyzed as described in Example 8 for tobacco.

EXAMPLE 10

Phytase activity assay

An amount of transgenic plant material was ground which in total contain approximately 0.25 PTU. (PTU=Phytase units. One unit of phytase activity is defined as that amount of enzyme which liberates inorganic phosphorus from 1.5 mM sodium phytate at the rate of 1 µmol/min at 37° C. and at pH 2.5). Alternatively, this amount of phytase may be extracted from the plant material.

The ground plant material was incubated in a total volume of 50 ml of a 250 mM glycine/HCl buffer pH 2.5 containing 0.86 g sodium phytate-11 $H_2O$. Although Aspergillus phytase expresses a pH optimum at 2.5 as well as at 5.5, the lower pH is chosen to exclude plant phytase activity.

The resulting mixture is incubated for 15 and 60 minutes at 37° C. The reaction is stopped by the addition of 5 ml from the incubate into 5 ml of 10% TCA (trichloroacetic acid). Thereafter, 10 ml of indicator reagent (3.66 g of $FeSO_2 \cdot 7H_2O$ in 50 ml of ammonium molybdate solution (2.5 g $(NH_4) 6Mo_7O_{24} \cdot 4H_2O$ and 8 ml conc. $H_2SO_4$, diluted up to 250 ml with demiwater) is added to the stopped enzyme solution. The intensity of the blue color is measured spectro-photometrically at 700 nm.

The inorganic phosphate content present at T=0 serves as a blank.

The measurements are indicative of the quantity of phosphate released in relation to a calibration curve of phosphate in the range of 0–1 mM.

EXAMPLE 11

Incubation of ground *Nicotiana tabacum* plant material with feedstuffs

In a typical experiment, 0.25 g of solvent extracted soybean meal is incubated with a quantity of ground *Nicotiana tabacum* plant material containing approximately 0.25 PTU as described above, except for the addition of sodium phytate. In this case, the added incubation agent consists of a mixture of 410 ml buffer and 90 ml of demiwater.

Figure 6:
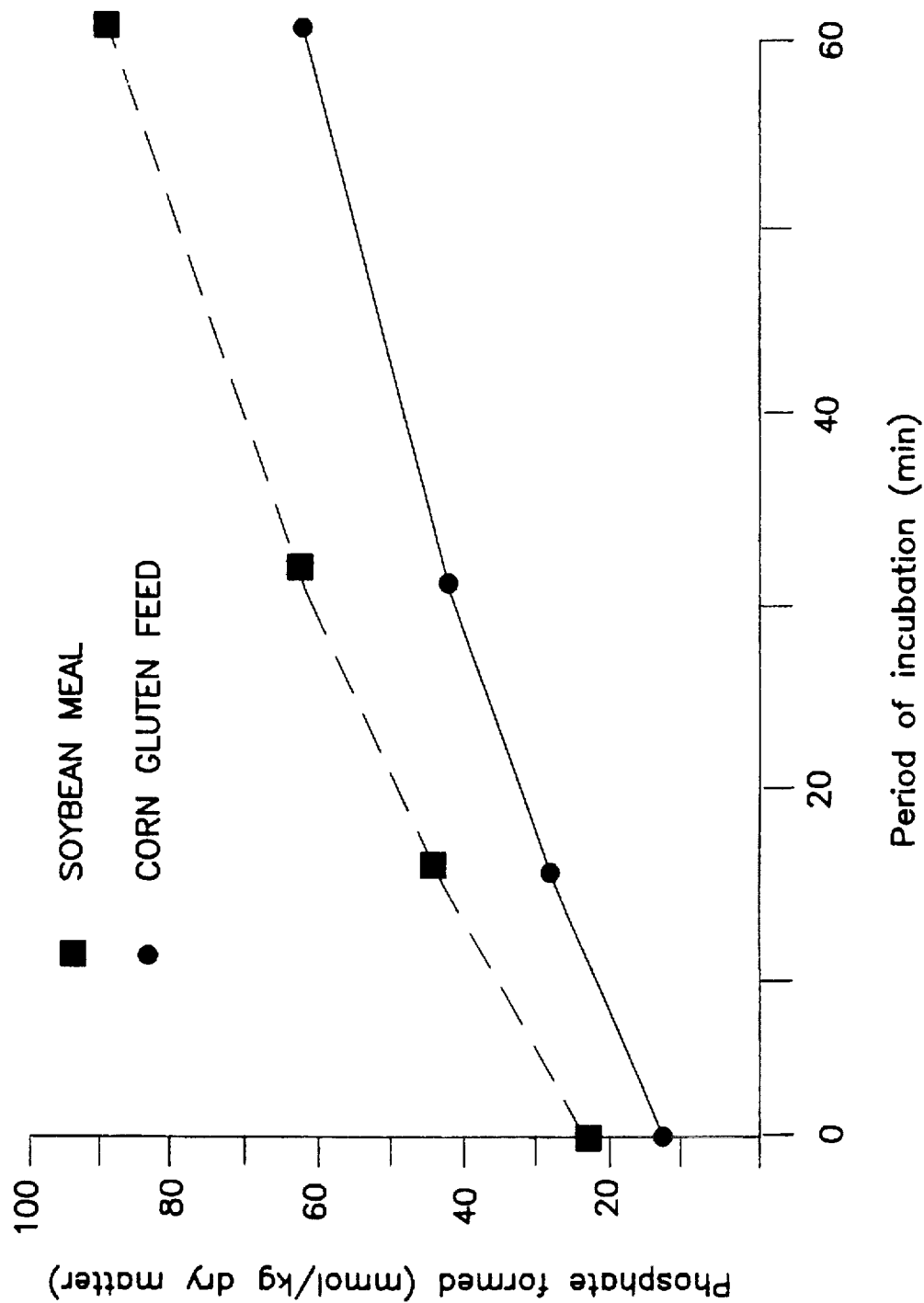
FIG. 6 is a graph showing the effects of the addition of ground seeds containing phytase on the liberation of inorganic phosphorous from phytate.

The liberation of phosphate from phytate in solvent extracted soybean meal is depicted in FIG. 6. Without added ground plant material, no activity is observed.

In a virtually identical experiment, similar results are obtained using maize gluten feed as a substrate. Results using transgenic seeds are shown in FIG. 6.

No activity is observed in the absence of ground plant material or when ground plant material are added which do not contain phytase activity.

EXAMPLE 12

In vitro testing of transgenic plant material containing phytase under conditions simulating the digestive tract of poultry To assess the effectivity of phytase produced in transgenic tobacco plant material, the activity of phytase from Aspergillus is determined in a model simulating the conditions found in the digestive tract in poultry.

A standard poultry feed sample is first incubated at 1 g/l ml demi water for 60 minutes at 39° C. to simulate the conditions in the crop of the animals. Subsequently, 5 ml of a pepsin solution (Merck: 5.28 g/l, pH 3.0—adjusted with HCl) is added, the pH adjusted with HCl to pH 3.0, and the incubation is continued for a further 90 minutes at the same temperature to simulate the conditions in the stomach.

During the incubation period, samples were taken in order to determine the amount of phosphate released from the phytate present in the feed.

Figure 7:
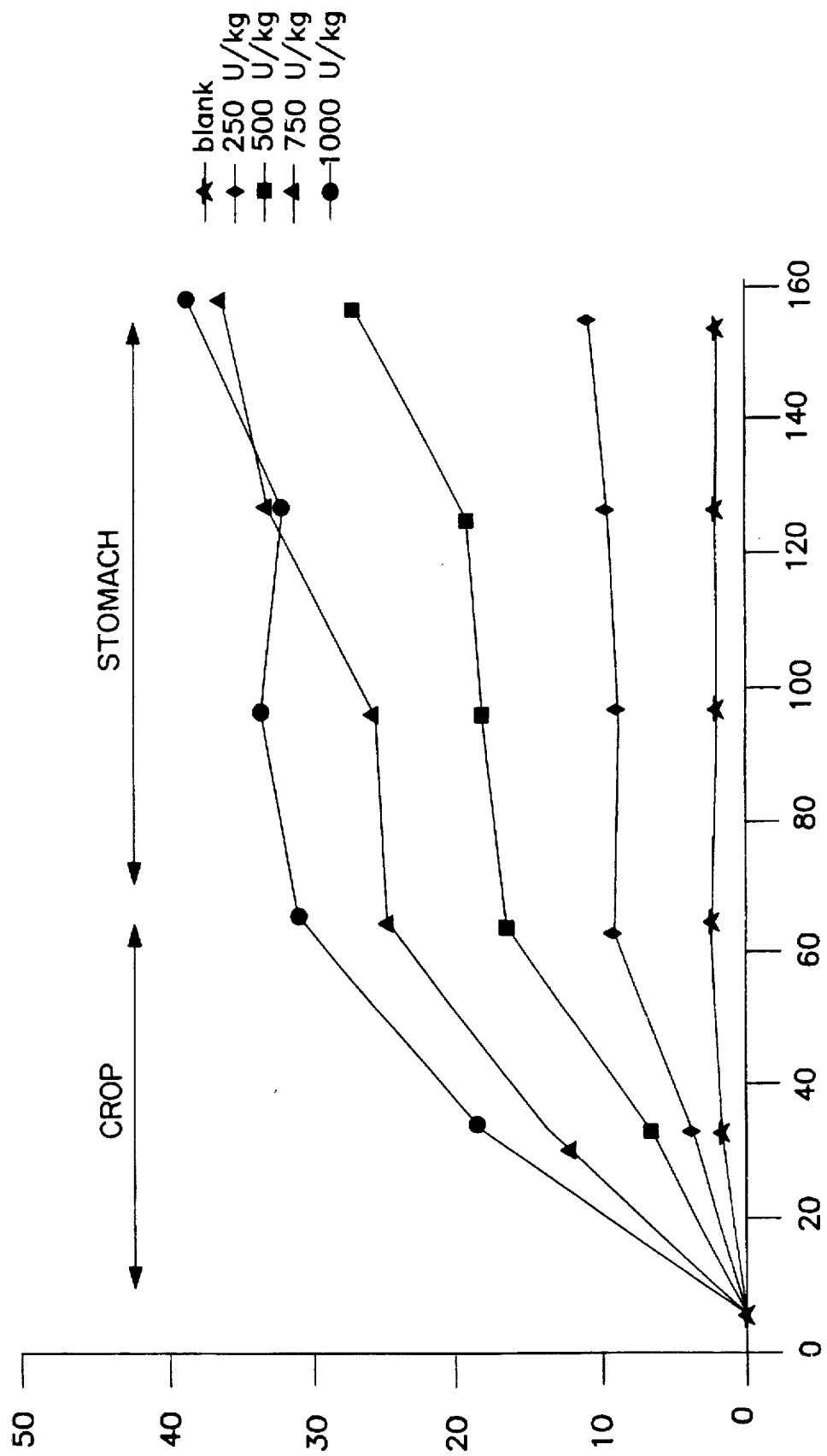
FIG. 7 is a graph showing dose-response relationship of Aspergillus phytase in an in vitro digestion model.

The action of fungal phytase is apparent from FIG. 7. Increasing the phytase dosage from 250 to 1000 PTU/kg feed results in an increased release of phosphate from the feed sample.

Figure 8:
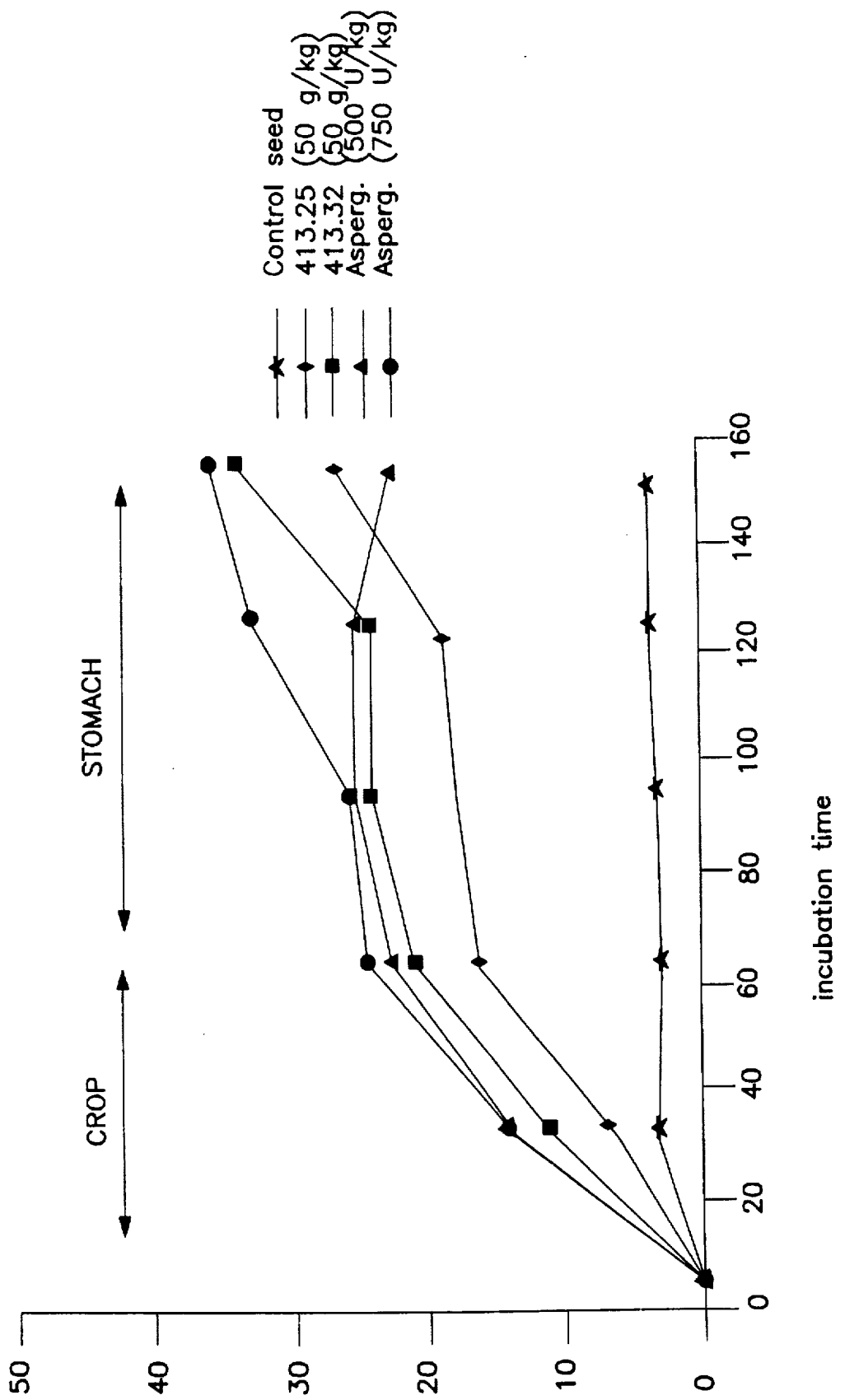
FIG. 8 is a graph showing dose-response relationship of Aspergillus phytase and phytase contained in tobacco seed in an in vitro digestion model.

When a sample of transgenic tobacco plant material, either seed or leaf (lines 413.25 and 413.32; after grinding in a mortar), is added in place of the fungal phytase, a similar increased phosphate release is observed (FIG. 8). Control tobacco plant material, which did not contain phytase, was also tested. No phosphate release was observed as compared to the blank control.

Comparison of the results with 50 g transgenic tobacco seed/kg feed with those obtained with 500 and 750 PTU/kg feed indicates that 1 g tobacco seed equals approximately 12 PTU in this in vitro poultry digestion model. A sample comparison using leaf material indicates that 1 g (fresh weight) of tobacco leaf material contains approximately 25 PTU.

EXAMPLE 13

Animal testing

Trials are carried out with broilers to show the efficacy of phytase expressed in plant seeds, as well as the absence of any negative effect of seeds from tobacco on zootechnical results.

Both phytase-expressing and control tobacco seed are harvested. Seeds were ground in 100 gram portions with a sieve (Retch-mill ZM1) having pores of 500 μm, taking care to keep the seeds cooled.

One day old male broiler chicks (Hybro) are housed in two tier battery cages (0.45 m²). The ambient temperature is 32° C. during the first two days and is decreased by 4° C. in the first week. Every following week, the temperature is decreased by 2° C. Broilers are reared in a one hour light and three hours dark regime.

The birds are vaccinated against New Castle Disease at one day of age using Clone 30 vaccine. During the experiments, the broilers are fed the experimental diets all mash and ad libitum. Growth and feed/gain ratios are measured during the experimental periods. Apparent availability of total phosphorus is measured in a three day period, during which feed consumption is measured as dry matter intake and excreta are collected quantitatively.

Apparent availability of phosphorus is defined as the difference between intake of phosphorus and excretion of phosphorus with the excreta.

The following control diets without addition of phytase are used:

| Diets | Ca (%) | total P (%) | phytate P (%) |
|---|---|---|---|
| 1 | 0.60 | 0.45 | 0.30 |
| 2 | 0.75 | 0.60 | 0.30 |
| 3 | 0.90 | 0.75 | 0.30 |

No graded feed phosphate is added to diet 1 (basal diet). Calcium and phosphorus from a mixture of anhydrous dicalcium phosphate and monoammonium phosphate (ratio 5:1) are supplemented to diets 2 and 3. All experimental diets are obtained by additions to the basal diet (see Table 1).

Experimental diet 4 contains microbial phytase at a concentration of 400 PTU/kg feed, prepared as described by Van Gorcom et al., supra.

Experimental diet 5 is like diet 4 but ground seeds of non-transgenic tobacco are added to the feed mixture to achieve a final ratio of 3 kg/90 kg feed.

Experimental diet 6 is also like diet 4 but 3 kg ground seeds of transgenic tobacco (line 413.25) are added to a mixture of 90 kg feed to obtain a final concentration of 400 PTU/kg feed.

The experiment is carried out with 176 broilers in 16 battery cages (11 per battery cage) until the age of 24 days. The treatments (diets) are repeated twice and are assigned randomly to the cages within each tier.

The availability of phosphorus is measured from 21–24 days of age.

The results with regard to phosphorous availability and growth of the animals supplied with diets 4, 5 and 6 each show the positive effect of the addition of phytase (Table 2). A comparison of diets 4, 5 and 6 also demonstrates that the inclusion of tobacco seeds in feed is compatible with the action of microbial phytase in the gastro-intestinal tract of farm animals such as broilers and shows no negative effect on the zootechnical results.

EXAMPLE 14

Storage stability of phytase produced in tobacco seeds

The storage stability of phytase produced in tobacco seeds were determined at various time intervals and at different storage temperatures.

Figure 9:
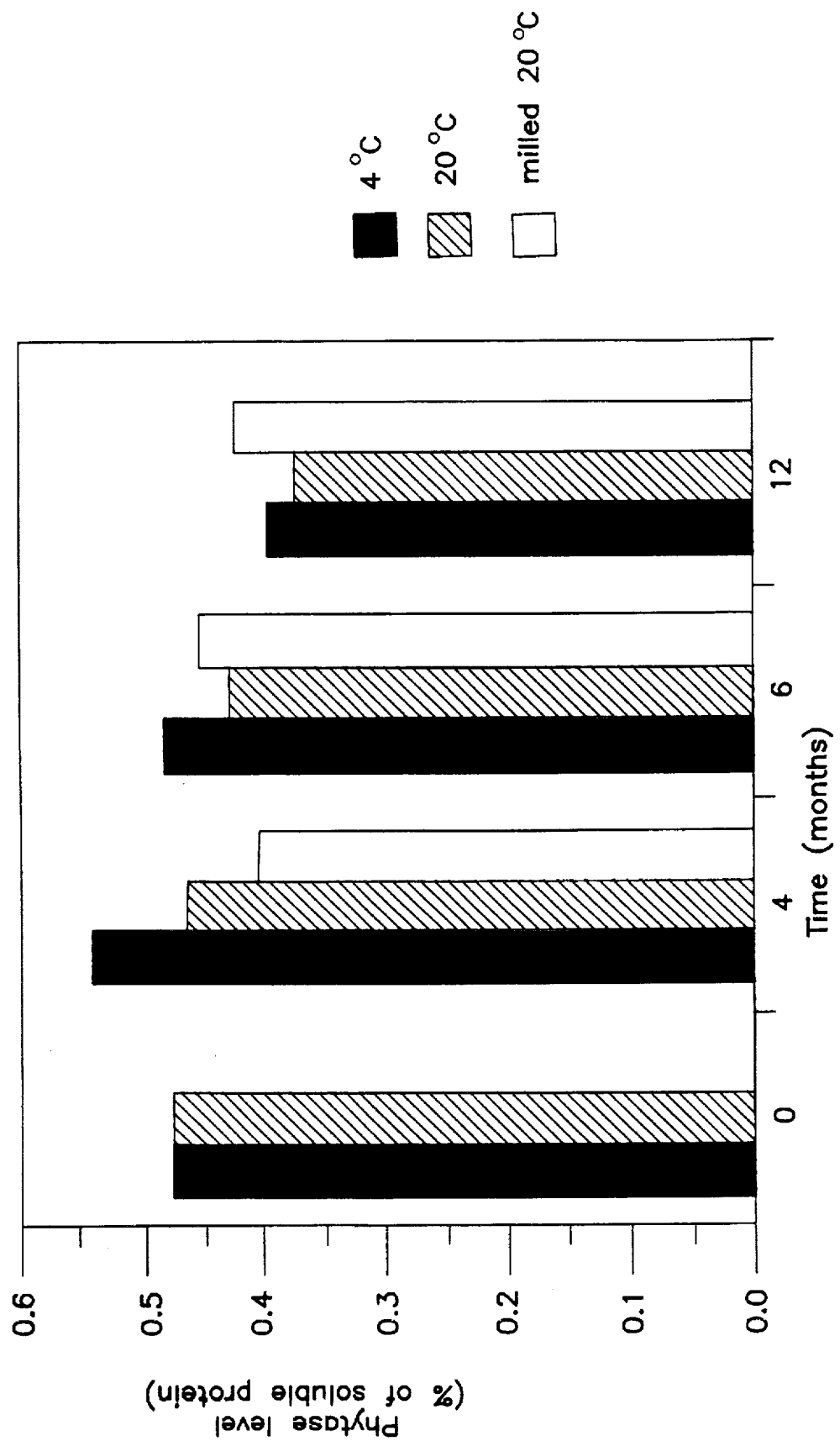
FIG. 9 is a histogram showing the storage stability of phytase produced in tobacco seeds.

Tobacco seeds of *Nicotiana tabacum* SR1 which has been transformed with the plasmid pMOG413 (see Example 6), in which phytase from *Aspergillus ficuum* was expressed extracellularly were stored at 4° C. and 20° C. Milled seeds were stored at 20° C. Phytase activity was determined at several time points. The enzyme appeared to be stable in whole, as well as in milled seeds (FIG. 9).

EXAMPLE 15

Expression of phytase under control of the ACP promoter
a) Isolation of a 0.6 kb BamHI/HindIII fragment comprising the terminator sequences from the *Agrobacterium tumefaciens* nopalin synthase (NOS) and the CaMV 35S genes The oligonucleotide duplex TCV11/12 was cloned in the HindIII site of pMOG29 (see Example 4).

TCV11/12:

5' AGCTCTGCAGTGAGGTACCA 3' (SEQ ID NO:9)
3' GACGTCACTCCATGGTTCGA 5' (SEQ ID NO:10)

The orientation of the adaptor TCV11/12 was checked by sequencing. A vector was used having the adaptor TCV11/12 in an orientation that would allow the cloning of the CaMV 35S terminator in a reverse orientation with respect to the *Agrobacterium tumefaciens* nopalin synthase (NOS) terminator sequence. In the resulting vector, linearized with PstI and KpnI, the 0.25 kb PstI/KpnI 35s terminator fragment isolated from plasmid pRT102 (Töpfer et al. (1987) Nucl. Acids Res. 15, 5890) was cloned. To destroy the PstI site, the obtained vector was linearized with PstI, blunted with Klenow polymerase, ligated and transformed to *E. coli*. From the resulting vector an 0.6 kb BamHI/HindIII fragment was isolated containing the terminator sequences from the *Agrobacterium tumefaciens* nopalin synthase (NOS) and the CaMV 35S genes, with the 35S terminator present in the reverse orientation.

b) Cloning and transformation of the binary vector

A 1 kb promoter of the seed-specific acyl carrier protein (ACP) gene from *Brassica napus* cv. Westar was synthesized by PCR as an EcoRI/NcoI fragment with isolated genomic DNA (Mettler, supra) as a template. Synthetic DNA primers ACPI and ACPII, based on the sequence published by de Silva, J. et al. ((1992) Plant Mol. Biol. 18, 1163–1172) were used in the PCR reaction.

ACPI   5'   CGCGAATTCTGCAGCCAGAAGGATAAAG 3' (SEQ ID NO:11)

ACPII  5'   GTGGTCGCCATGGTCGATATTCACG 3' (SEQ ID NO:12)

The EcoRI/NcoI fragment was cloned in pUC18, linearized with EcoRI and BamHI in a three-way ligation with the oligonucleotide duplex Trans1/2, encoding the signal peptide of the tobacco PR-S protein.

Trans1/2:

5'   CATGAACTTCCTCAAGAGCTTCCCCTTTTATGCCTTCCTTTGTTTTG(SEQ ID NO:13)
3'           TTGAAGGAGTTCTCGAAGGGGAAAATACGGAAGGAAACAAAA(SEQ ID NO:14)

GCCAATACTTTGTAGCTGTTACGCATGCTCGAG 3' (SEQ ID NO:15)
CCGGTTATGAAACATCGACAATGCGTACGAGCTCCTAG 5' (SEQ ID NO:16)

Figure 10:
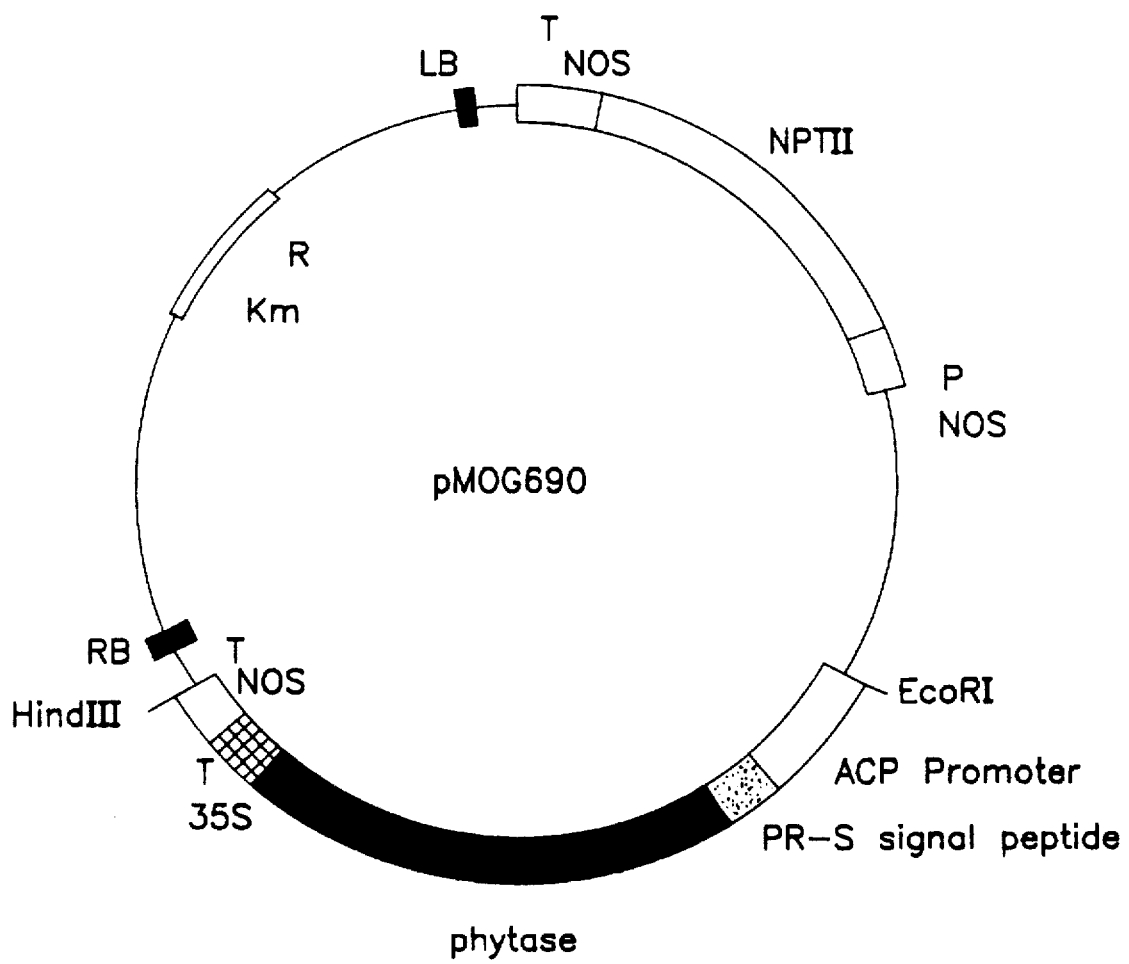
FIG. 10 is a diagram of plasmid pMOG690. Binary vector containing the phytase gene under control of the ACP promoter.

In the resulting vector, cut with SphI and BamHI, the phytase encoding cDNA fragment, isolated from pMOG417 (see Example 4) by digestion with SphI and BamHI (partial), was cloned. In this vector, linearized with BamHI (partial) and HindIII, an 0.6 kb DNA fragment containing the terminator sequences from the *Agrobacterium tumefaciens* nopalin synthase (NOS) and the CaMV 35S genes (with the 35S terminator present in the reverse orientation) was cloned. From the resulting vector, the 3.2 kb EcoRI/HindIII expression cassette was cloned into binary vector pMOG402 cut with EcoRI and HindIII. The resulting binary plasmid, designated pMOG690 (FIG. 10), was mobilized in a triparental mating with the *E. coli* strain HB101 containing plasmid pRK2013 (Ditta et al., supra), into Agrobacterium strain MOG101, which contains a plasmid having the virulence genes necessary for T-DNA transfer to the plant (Hoekema et al., 1983, supra). Tobacco was transformed as described in Example 6. Transgenic seeds were harvested and assayed for phytase activity as described (see Example 10). The average expression level was 0.03% of soluble protein for 6 plants tested.

EXAMPLE 16

Expression of phytase under control of a 3 kb cruciferin promoter

A 3 kb promoter fragment of a cruciferin gene of *Brassica napus* cv. Jet Neuf was used to control the expression of the phytase gene. The promoter fragment was fused to a DNA fragment encoding the AMV RNA4 leader, the tobacco PR-S signal peptide, mature phytase and the terminator sequences from the Agrobacterium nopalin synthase (NOS) and the CaMV 35S genes.

Isolated genomic DNA of *Brassica napus* cv. Jet Neuf was digested with SalI and BamHI, run on an agarose gel, blotted and hybridized with the PCR fragment comprising the 5' flanking region of the cruciferin A (cruA) gene (see Example 7). Southern hybridization showed a strongly hybridizing fragment of about 2.8 kb. *Brassica napus* cv. Jet Neuf DNA, digested with SalI and BamHI was size-fractionated on a 10%–20% sucrose gradient. The fraction containing DNA fragments of approximately 2.5–3.2 kb was ligated in plasmid pGEM4 (Promega), linearized with SalI and BamHI. This ligation was transformed to *E. coli* strain DH10$^B$ (Gibco BRL), resulting in a partial genomic DNA library of about 100,000 clones. This library was screened with the PCR fragment of the cruA gene (see above) as a probe. One positive clone, designated pMOGcru, was found to contain a fragment that in the corresponding part was more than 95% identical with the cruA promoter sequence published by Ryan et al. (supra).

A set of synthetic oligonucleotides, TCV9 and TCV10 were used to synthesize by PCR technology a fragment consisting of the distal 13 bp of the cruA promoter from the PvuII site to the RNA start site followed by the RNA4 leader sequence of alfalfa mosaic virus (AMV) and the signal peptide-encoding sequence of the tobacco PR-S protein using plasmid pMOG417 (see Example 4) as a template.

TCV9   5'   CAGAGCATGCGTAACAGCTAC                                3'(SEQ ID NO:17)
TCV10  5'   CGGAATTCGGCAGCTGTAAGACCAGAGGGTTTTTATTTTTA 3'(SEQ ID NO:18)

The thus-obtained 123 bp PCR fragment was cloned in a pGEM4 vector lacking the PvuII site (The PvuII site was destroyed by, in sequence, overdigestion of pGEM4 with PvuII, ligation, digestion with PvuII, transformation to *E. coli*, and screening for clones lacking the PvuII site), linearized with EcoRI and SphI. The resulting vector was linearized with EcoRI and PvuII, and used in a three-way ligation containing additionally a 0.1 kb SalI/PvuII cruA promoter fragment from plasmid pMOG428 (see Example 7) and the 2.8 kb EcoRI/SalI cruciferin promoter fragment from pMOGcru (see above). In the obtained vector, cut with SphI and BamHI, the 1.5 kb cDNA fragment from pMOG417 encoding phytase (see Example 4), obtained by digestion with SphI and BamHI (partial), was cloned. In the resulting vector, linearized with BamHI (partial) and HindIII, an 0.6 kb DNA fragment consisting of the terminator sequences from the Agrobacterium nopalin synthase (NOS) and the CaMV 35S genes was cloned. The CaMV 35S terminator was present in the reverse orientation (see Example 15). The 5.2 kb expression cassette was cut out with EcoRI and HindIII (partial), and cloned into binary vector pMOG402 cut with EcoRI and HindIII.

Figure 11:
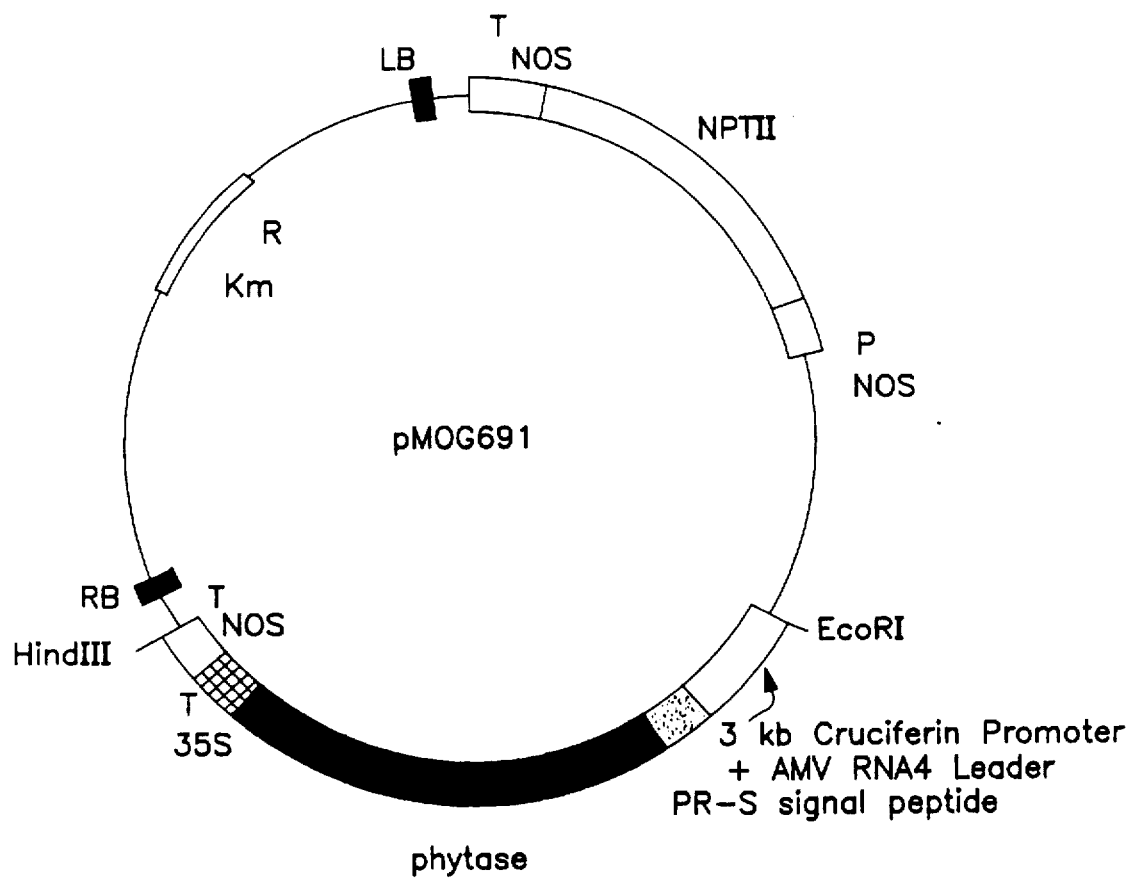
FIG. 11 is a diagram of plasmid pMOG691 containing the phytase gene under control of a 3 kb cruciferin promoter.

The resulting binary plasmid, designated pMOG691 (FIG. 11), was mobilized in a triparental mating with the *E. coli* strain HB101 containing plasmid pRK2013 (Ditta et al., 1980), into Agrobacterium strain MOG101, which contains a plasmid having the virulence genes necessary for T-DNA transfer to the plant (Hoekema et al., 1983). Tobacco was transformed as described in Example 6. Transgenic seeds were harvested and assayed for phytase activity as described (see Example 10). The average expression level was 0.3% of soluble protein for 9 plants tested.

While the present invention has been described with reference to specific embodiments thereof, it should be understood by those skilled in the art that various changes may be made and equivalents may be substituted without parting from the true spirit and scope of the invention. In addition, many modifications may be made to adapt a particular situation, material, plant, seed, process, process step or steps to the object, spirit and scope of the invention. All such modifications are intended to be within the scope of the claims appended hereto.

TABLE 1

Composition of basal diet in experiments with broilers

| Ingredients | Contents (g/kg) |
|---|---|
| Yellow maize | 280.0 |
| Sorghum (low tannin) | 200.0 |
| Sunflower seed meal (solv. extr.) | 80.0 |
| Soya bean meal (solvent extr., 48.8% protein) | 350.0 |
| Soya bean oil | 58.5 |
| Vitamins* | 5.0 |
| Minerals* | 15.0 |
| Limestone | 1.0 |
| Synth. methionine | 1.0 |
| $Cr_2O_3$ | 0.5 |
| | 1001.0 |
| ME (MJ/kg) | 13.1 |
| Lysine | 12.9 |
| Methionine + cystine | 9.1 |
| Calcium | 6.0 (6.0–6.6)** |
| Total phosphorus | 4.5 (4.7–4.7)** |
| Organic phytic phosporus | 3.0 (3.1–3.1)** |

*Amount supplied per kg diet: 12000 IU vitamin A; 2000 IU vitamin $D_3$; 5 IU vitamin E; 1.5 mg vitamin $K_3$; 1 mg thiamins; 5 mg riboflavin; 1 mg pyridoxine; 30 mg nicotinic acid, 7.5 mg D-pantothenic acid; 0.015 mg vitamin $B_{12}$; 0.5 mg folic acid; 350 mg choline chloride; 75 mg ethoxyquin; 9.5 g $CaCO_3$; 2.5 g NaCl; 0.26 g $FeSO_4$; 0.24 g $MnSO_4$; 45 mg $CuSO_4$; 60 mg $ZnSO_4$; 105 mg KI mixture.
**( ) Analyzed for experiments 1 and 2 respectively.

TABLE 2

Effect of Phytase on the Apparent Availability of Total P and Ca, the P Content in Manure and the Performance of Broilers

| Diets | Ca/P (g/kg) | Added phytase (units/kg) | Availability (%) 21–24 d P | Availability (%) 21–24 d Ca | Amount of P in manure (g) per kg dm feed intake | Growth 0–24 d (g) |
|---|---|---|---|---|---|---|
| 1 | 6/4.5 | 0 | 49.8 | 47.2 | 2.7 | 338 |
| 2 | 7.5/6 | 0 | 45.6 | 48.9 | 3.8 | 592 |
| 3 | 9/7.5 | 0 | 44.6 | 46.9 | 4.9 | 683 |
| 4 | as 1 | 400 | 60.5 | 58.6 | 2.1 | 620 |
| 5 | as 1 | 0 | 48.5 | 48.0 | 2.7 | 340 |
| 6 | as 1 | 400 | 60.2 | 59.3 | 2.1 | 615 |

We claim:

1. A recombinant expression system capable, when contained in a higher plant cell or the cells of an intact higher plant, of expressing a first nucleotide sequence encoding a microbial protein which catalyzes the liberation of inorganic phosphate from myo-inositol hexakis-phosphate, said expression system comprising said first nucleotide sequence encoding said protein operably linked to transcription controlling nucleotide sequences operable in a higher plant cell or in the cells of a higher plant.

2. The expression system of claim 1 wherein the microbial protein is a fungal protein.

3. The expression system of claim 2 wherein the fungal protein is of the genus Aspergillus.

4. The expression system of claim 1 wherein said first nucleotide sequence is preceded by a second nucleotide sequence encoding a signal peptide operably linked to said protein.

5. The expression system of claim 4 wherein said signal peptide is the PR protein PR-S signal peptide from tobacco.

6. The expression system of claim 1 wherein the control sequences comprise a constitutive promoter.

7. The expression system of claim 1 wherein the control sequences comprise a tissue-specific promoter.

8. A transfer vector which comprises the expression system of claim 1.

9. Bacterial cells modified to contain the expression system of claim 1.

10. Higher plant cells or the cells of plant parts or intact plants modified to contain the expression system of claim 1.

11. A method to produce a microbial phytase in a plant cell, plank part or plant according to claim 10, which method comprises culturing the plant cell, plant part or plant of claim 10 under conditions wherein said first nucleotide sequence is expressed; and converting said plant cells, plant parts or plants into a composition suitable for animal feed.

12. A feed composition for animals which composition comprises the plant cells, plant parts or plants of claim 10 in admixture with animal food.

13. A method to promote the growth of an animal and reduce the level of phytate in the feces of said animal, which method comprises feeding said animal the feed composition of claim 12.

* * * * *

SEQUENCE LISTING ( 1 ) GENERAL INFORMATION:

( i i i ) NUMBER OF SEQUENCES: 31

( 2 ) INFORMATION FOR SEQ ID NO:1:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:1:

GGGTAGAATT CAAAAATGGG CGTCTCTGCT GTTCTA    36

( 2 ) INFORMATION FOR SEQ ID NO:2:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

AGTGACGAAT TCGTGCTGGT GGAGATGGTG TCG            33

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

GAGCACCAAG CTGAAGGATC C            21

( 2 ) INFORMATION FOR SEQ ID NO:4:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

AAACTGCAGG CGTTGAGTGT GATTGTTTAA AGGG            34

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

GTTCGGAATT CGGGTTCCGG            20

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

AACTGTTGAG CTGTAGAGCC            20

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

CTTAAGATCT TACCCAGTGA            20

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

CGGAGAAGCT TGCATCTCGT 20

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

AGCTCTGCAG TGAGGTACCA 20

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

AGCTTGGTAC CTCACTGCAG 20

( 2 ) INFORMATION FOR SEQ ID NO:11:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

CGCGAATTCT GCAGCCAGAA GGATAAAG 28

( 2 ) INFORMATION FOR SEQ ID NO:12:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

GTGGTCGCCA TGGTCGATAT TCACG 25

( 2 ) INFORMATION FOR SEQ ID NO:13:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

CATGAACTTC CTCAAGAGCT TCCCCTTTTA TGCCTTCCTT TGTTTTG 47

( 2 ) INFORMATION FOR SEQ ID NO:14:

(i) SEQUENCE CHARACTERISTICS:
    (A) LENGTH: 42 base pairs
    (B) TYPE: nucleic acid
    (C) STRANDEDNESS: single
    (D) TOPOLOGY: linear (xi) SEQUENCE DESCRIPTION: SEQ ID NO:14:

AAAACAAAGG AAGGCATAAA AGGGGAAGCT CTTGAGGAAG TT    42

(2) INFORMATION FOR SEQ ID NO:15:

(i) SEQUENCE CHARACTERISTICS:
    (A) LENGTH: 33 base pairs
    (B) TYPE: nucleic acid
    (C) STRANDEDNESS: single
    (D) TOPOLOGY: linear (xi) SEQUENCE DESCRIPTION: SEQ ID NO:15:

GCCAATACTT TGTAGCTGTT ACGCATGCTC GAG    33

(2) INFORMATION FOR SEQ ID NO:16:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (xi) SEQUENCE DESCRIPTION: SEQ ID NO:16:

GATCCTCGAG CATGCGTAAC AGCTACAAAG TATTGGCC    38

(2) INFORMATION FOR SEQ ID NO:17:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (xi) SEQUENCE DESCRIPTION: SEQ ID NO:17:

CAGAGCATGC GTAACAGCTA C    21

(2) INFORMATION FOR SEQ ID NO:18:

(i) SEQUENCE CHARACTERISTICS:
    (A) LENGTH: 41 base pairs
    (B) TYPE: nucleic acid
    (C) STRANDEDNESS: single
    (D) TOPOLOGY: linear (xi) SEQUENCE DESCRIPTION: SEQ ID NO:18:

CGGAATTCGG CAGCTGTAAG ACCAGAGGGT TTTTATTTTT A    41

(2) INFORMATION FOR SEQ ID NO:19:

(i) SEQUENCE CHARACTERISTICS:
    (A) LENGTH: 1404 base pairs
    (B) TYPE: nucleic acid
    (C) STRANDEDNESS: single
    (D) TOPOLOGY: linear (ix) FEATURE:
    (A) NAME/KEY: CDS
    (B) LOCATION: 1..1401

(ix) FEATURE:
    (A) NAME/KEY: mat_peptide
    (B) LOCATION: 70

(xi) SEQUENCE DESCRIPTION: SEQ ID NO:19:

```
ATG GGC GTC TCT GCT GTT CTA CTT CCT TTG TAT CTC CTG TCT GGA GTC        48
Met Gly Val Ser Ala Val Leu Leu Pro Leu Tyr Leu Leu Ser Gly Val
-23             -20                 -15                 -10

ACC TCC GGA CTG GCA GTC CCC GCC TCG AGA AAT CAA TCC AGT TGC GAT        96
Thr Ser Gly Leu Ala Val Pro Ala Ser Arg Asn Gln Ser Ser Cys Asp
        -5                      1                   5

ACG GTC GAT CAG GGG TAT CAA TGC TTC TCC GAG ACT TCG CAT CTT TGG       144
Thr Val Asp Gln Gly Tyr Gln Cys Phe Ser Glu Thr Ser His Leu Trp
 10              15                  20                      25

GGT CAA TAC GCA CCG TTC TTC TCT CTG GCA AAC GAA TCG GTC ATC TCC       192
Gly Gln Tyr Ala Pro Phe Phe Ser Leu Ala Asn Glu Ser Val Ile Ser
                 30                  35                  40

CCT GAG GTG CCC GCC GGA TGC AGA GTC ACT TTC GCT CAG GTC CTC TCC       240
Pro Glu Val Pro Ala Gly Cys Arg Val Thr Phe Ala Gln Val Leu Ser
             45                  50                  55

CGT CAT GGA GCG CGG TAT CCG ACC GAC TCC AAG GGC AAG AAA TAC TCC       288
Arg His Gly Ala Arg Tyr Pro Thr Asp Ser Lys Gly Lys Lys Tyr Ser
         60                  65                  70

GCT CTC ATT GAG GAG ATC CAG CAG AAC GCG ACC ACC TTT GAC GGA AAA       336
Ala Leu Ile Glu Glu Ile Gln Gln Asn Ala Thr Thr Phe Asp Gly Lys
     75                  80                  85

TAT GCC TTC CTG AAG ACA TAC AAC TAC AGC TTG GGT GCA GAT GAC CTG       384
Tyr Ala Phe Leu Lys Thr Tyr Asn Tyr Ser Leu Gly Ala Asp Asp Leu
 90                  95                 100                     105

ACT CCC TTC GGA GAA CAG GAG CTA GTC AAC TCC GGC ATC AAG TTC TAC       432
Thr Pro Phe Gly Glu Gln Glu Leu Val Asn Ser Gly Ile Lys Phe Tyr
                 110                 115                 120

CAG CGG TAC GAA TCG CTC ACA AGG AAC ATC GTT CCA TTC ATC CGA TCC       480
Gln Arg Tyr Glu Ser Leu Thr Arg Asn Ile Val Pro Phe Ile Arg Ser
             125                 130                 135

TCT GGC TCC AGC CGC GTG ATC GCC TCC GGC AAG AAA TTC ATC GAG GGC       528
Ser Gly Ser Ser Arg Val Ile Ala Ser Gly Lys Lys Phe Ile Glu Gly
         140                 145                 150

TTC CAG AGC ACC AAG CTG AAG GAT CCT CGT GCC CAG CCC GGC CAA TCG       576
Phe Gln Ser Thr Lys Leu Lys Asp Pro Arg Ala Gln Pro Gly Gln Ser
     155                 160                 165

TCG CCC AAG ATC GAC GTG GTC ATT TCC GAG GCC AGC TCA TCC AAC AAC       624
Ser Pro Lys Ile Asp Val Val Ile Ser Glu Ala Ser Ser Ser Asn Asn
170                 175                 180                 185

ACT CTC GAC CCA GGC ACC TGC ACT GTC TTC GAA GAC AGC GAA TTG GCC       672
Thr Leu Asp Pro Gly Thr Cys Thr Val Phe Glu Asp Ser Glu Leu Ala
                 190                 195                 200

GAT ACC GTC GAA GCC AAT TTC ACC GCC ACG TTC GTC CCC TCC ATT CGT       720
Asp Thr Val Glu Ala Asn Phe Thr Ala Thr Phe Val Pro Ser Ile Arg
             205                 210                 215

CAA CGT CTG GAG AAC GAC CTG TCC GGT GTG ACT CTC ACA GAC ACA GAA       768
Gln Arg Leu Glu Asn Asp Leu Ser Gly Val Thr Leu Thr Asp Thr Glu
         220                 225                 230

GTG ACC TAC CTC ATG GAC ATG TGC TCC TTC GAC ACC ATC TCC ACC AGC       816
Val Thr Tyr Leu Met Asp Met Cys Ser Phe Asp Thr Ile Ser Thr Ser
     235                 240                 245

ACC GTC GAC ACC AAG CTG TCC CCC TTC TGT GAC CTG TTC ACC CAT GAC       864
Thr Val Asp Thr Lys Leu Ser Pro Phe Cys Asp Leu Phe Thr His Asp
250                 255                 260                 265

GAA TGG ATC AAC TAC GAC TAC CTC CAG TCC TTG AAA AAG TAT TAC GGC       912
Glu Trp Ile Asn Tyr Asp Tyr Leu Gln Ser Leu Lys Lys Tyr Tyr Gly
                 270                 275                 280

CAT GGT GCA GGT AAC CCG CTC GGC CCG ACC CAG GGC GTC GGC TAC GCT       960
His Gly Ala Gly Asn Pro Leu Gly Pro Thr Gln Gly Val Gly Tyr Ala
             285                 290                 295
```

```
AAC  GAG  CTC  ATC  GCC  CGT  CTG  ACC  CAC  TCG  CCT  GTC  CAC  GAT  GAC  ACC    1008
Asn  Glu  Leu  Ile  Ala  Arg  Leu  Thr  His  Ser  Pro  Val  His  Asp  Asp  Thr
          300                      305                     310

AGT  TCC  AAC  CAC  ACT  TTG  GAC  TCG  AGC  CCG  GCT  ACC  TTT  CCG  CTC  AAC    1056
Ser  Ser  Asn  His  Thr  Leu  Asp  Ser  Ser  Pro  Ala  Thr  Phe  Pro  Leu  Asn
          315                      320                     325

TCT  ACT  CTC  TAC  GCG  GAC  TTT  TCG  CAT  GAC  AAC  GGC  ATC  ATC  TCC  ATT    1104
Ser  Thr  Leu  Tyr  Ala  Asp  Phe  Ser  His  Asp  Asn  Gly  Ile  Ile  Ser  Ile
330                      335                     340                         345

CTC  TTT  GCT  TTA  GGT  CTG  TAC  AAC  GGC  ACT  AAG  CCG  CTA  TCT  ACC  ACG    1152
Leu  Phe  Ala  Leu  Gly  Leu  Tyr  Asn  Gly  Thr  Lys  Pro  Leu  Ser  Thr  Thr
                    350                      355                     360

ACC  GTG  GAG  AAT  ATC  ACC  CAG  ACA  GAT  GGA  TTC  TCG  TCT  GCT  TGG  ACG    1200
Thr  Val  Glu  Asn  Ile  Thr  Gln  Thr  Asp  Gly  Phe  Ser  Ser  Ala  Trp  Thr
               365                      370                     375

GTT  CCG  TTT  GCT  TCG  CGT  TTG  TAC  GTC  GAG  ATG  ATG  CAG  TGT  CAG  GCG    1248
Val  Pro  Phe  Ala  Ser  Arg  Leu  Tyr  Val  Glu  Met  Met  Gln  Cys  Gln  Ala
          380                      385                     390

GAG  CAG  GAG  CCG  CTG  GTC  CGT  GTC  TTG  GTT  AAT  GAT  CGC  GTT  GTC  CCG    1296
Glu  Gln  Glu  Pro  Leu  Val  Arg  Val  Leu  Val  Asn  Asp  Arg  Val  Val  Pro
     395                      400                     405

CTG  CAT  GGG  TGT  CCG  GTT  GAT  GCT  TTG  GGG  AGA  TGT  ACC  CGG  GAT  AGC    1344
Leu  His  Gly  Cys  Pro  Val  Asp  Ala  Leu  Gly  Arg  Cys  Thr  Arg  Asp  Ser
410                      415                     420                         425

TTT  GTG  AGG  GGG  TTG  AGC  TTT  GCT  AGA  TCT  GGG  GGT  GAT  TGG  GCG  GAG    1392
Phe  Val  Arg  Gly  Leu  Ser  Phe  Ala  Arg  Ser  Gly  Gly  Asp  Trp  Ala  Glu
                    430                      435                     440

TGT  TTT  GCT  TAG                                                                1404
Cys  Phe  Ala
```

( 2 ) INFORMATION FOR SEQ ID NO:20:

( i ) SEQUENCE CHARACTERISTICS:
        ( A ) LENGTH: 467 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

```
Met  Gly  Val  Ser  Ala  Val  Leu  Leu  Pro  Leu  Tyr  Leu  Leu  Ser  Gly  Val
-23            -20                      -15                      -10

Thr  Ser  Gly  Leu  Ala  Val  Pro  Ala  Ser  Arg  Asn  Gln  Ser  Ser  Cys  Asp
          -5                       1                  5

Thr  Val  Asp  Gln  Gly  Tyr  Gln  Cys  Phe  Ser  Glu  Thr  Ser  His  Leu  Trp
10                       15                  20                            25

Gly  Gln  Tyr  Ala  Pro  Phe  Phe  Ser  Leu  Ala  Asn  Glu  Ser  Val  Ile  Ser
                    30                       35                            40

Pro  Glu  Val  Pro  Ala  Gly  Cys  Arg  Val  Thr  Phe  Ala  Gln  Val  Leu  Ser
               45                       50                  55

Arg  His  Gly  Ala  Arg  Tyr  Pro  Thr  Asp  Ser  Lys  Gly  Lys  Lys  Tyr  Ser
               60                       65                  70

Ala  Leu  Ile  Glu  Glu  Ile  Gln  Gln  Asn  Ala  Thr  Thr  Phe  Asp  Gly  Lys
     75                       80                  85

Tyr  Ala  Phe  Leu  Lys  Thr  Tyr  Asn  Tyr  Ser  Leu  Gly  Ala  Asp  Asp  Leu
90                       95                  100                          105

Thr  Pro  Phe  Gly  Glu  Gln  Glu  Leu  Val  Asn  Ser  Gly  Ile  Lys  Phe  Tyr
                    110                      115                     120

Gln  Arg  Tyr  Glu  Ser  Leu  Thr  Arg  Asn  Ile  Val  Pro  Phe  Ile  Arg  Ser
```

|     |     |     |     |     |     |     |     |     |     |     |     |     |     |     |
|---|---|---|---|---|---|---|---|---|---|---|---|---|---|---|
|  |  |  |  | 125 |  |  |  | 130 |  |  |  | 135 |  |  |
| Ser | Gly | Ser | Ser | Arg | Val | Ile | Ala | Ser | Gly | Lys | Lys | Phe | Ile | Glu | Gly |
|  |  | 140 |  |  |  | 145 |  |  |  | 150 |  |  |  |  |  |
| Phe | Gln | Ser | Thr | Lys | Leu | Lys | Asp | Pro | Arg | Ala | Gln | Pro | Gly | Gln | Ser |
|  |  | 155 |  |  |  | 160 |  |  |  | 165 |  |  |  |  |  |
| Ser | Pro | Lys | Ile | Asp | Val | Val | Ile | Ser | Glu | Ala | Ser | Ser | Ser | Asn | Asn |
| 170 |  |  |  |  | 175 |  |  |  | 180 |  |  |  |  |  | 185 |
| Thr | Leu | Asp | Pro | Gly | Thr | Cys | Thr | Val | Phe | Glu | Asp | Ser | Glu | Leu | Ala |
|  |  |  |  | 190 |  |  |  | 195 |  |  |  |  |  | 200 |  |
| Asp | Thr | Val | Glu | Ala | Asn | Phe | Thr | Ala | Thr | Phe | Val | Pro | Ser | Ile | Arg |
|  |  |  | 205 |  |  |  | 210 |  |  |  |  |  | 215 |  |  |
| Gln | Arg | Leu | Glu | Asn | Asp | Leu | Ser | Gly | Val | Thr | Leu | Thr | Asp | Thr | Glu |
|  |  | 220 |  |  |  |  | 225 |  |  |  |  | 230 |  |  |  |
| Val | Thr | Tyr | Leu | Met | Asp | Met | Cys | Ser | Phe | Asp | Thr | Ile | Ser | Thr | Ser |
|  | 235 |  |  |  |  | 240 |  |  |  |  | 245 |  |  |  |  |
| Thr | Val | Asp | Thr | Lys | Leu | Ser | Pro | Phe | Cys | Asp | Leu | Phe | Thr | His | Asp |
| 250 |  |  |  |  | 255 |  |  |  | 260 |  |  |  |  |  | 265 |
| Glu | Trp | Ile | Asn | Tyr | Asp | Tyr | Leu | Gln | Ser | Leu | Lys | Lys | Tyr | Tyr | Gly |
|  |  |  |  | 270 |  |  |  | 275 |  |  |  |  |  | 280 |  |
| His | Gly | Ala | Gly | Asn | Pro | Leu | Gly | Pro | Thr | Gln | Gly | Val | Gly | Tyr | Ala |
|  |  |  | 285 |  |  |  |  | 290 |  |  |  |  | 295 |  |  |
| Asn | Glu | Leu | Ile | Ala | Arg | Leu | Thr | His | Ser | Pro | Val | His | Asp | Asp | Thr |
|  |  |  | 300 |  |  |  | 305 |  |  |  |  | 310 |  |  |  |
| Ser | Ser | Asn | His | Thr | Leu | Asp | Ser | Ser | Pro | Ala | Thr | Phe | Pro | Leu | Asn |
|  | 315 |  |  |  |  | 320 |  |  |  |  | 325 |  |  |  |  |
| Ser | Thr | Leu | Tyr | Ala | Asp | Phe | Ser | His | Asp | Asn | Gly | Ile | Ile | Ser | Ile |
| 330 |  |  |  |  | 335 |  |  |  | 340 |  |  |  |  |  | 345 |
| Leu | Phe | Ala | Leu | Gly | Leu | Tyr | Asn | Gly | Thr | Lys | Pro | Leu | Ser | Thr | Thr |
|  |  |  |  | 350 |  |  |  | 355 |  |  |  |  |  | 360 |  |
| Thr | Val | Glu | Asn | Ile | Thr | Gln | Thr | Asp | Gly | Phe | Ser | Ser | Ala | Trp | Thr |
|  |  |  | 365 |  |  |  | 370 |  |  |  |  |  | 375 |  |  |
| Val | Pro | Phe | Ala | Ser | Arg | Leu | Tyr | Val | Glu | Met | Met | Gln | Cys | Gln | Ala |
|  |  | 380 |  |  |  | 385 |  |  |  |  | 390 |  |  |  |  |
| Glu | Gln | Glu | Pro | Leu | Val | Arg | Val | Leu | Val | Asn | Asp | Arg | Val | Val | Pro |
|  | 395 |  |  |  |  | 400 |  |  |  |  | 405 |  |  |  |  |
| Leu | His | Gly | Cys | Pro | Val | Asp | Ala | Leu | Gly | Arg | Cys | Thr | Arg | Asp | Ser |
| 410 |  |  |  |  | 415 |  |  |  | 420 |  |  |  |  |  | 425 |
| Phe | Val | Arg | Gly | Leu | Ser | Phe | Ala | Arg | Ser | Gly | Gly | Asp | Trp | Ala | Glu |
|  |  |  |  | 430 |  |  |  | 435 |  |  |  |  |  | 440 |  |
| Cys | Phe | Ala |  |  |  |  |  |  |  |  |  |  |  |  |  |

( 2 ) INFORMATION FOR SEQ ID NO:21:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

```
GGAATTCTGG TACCTCCCGG GAGGATCCAT CTAGAGCTCG AGTAAGCTTC          50
```

( 2 ) INFORMATION FOR SEQ ID NO:22:

( i ) SEQUENCE CHARACTERISTICS:
        ( A ) LENGTH: 54 base pairs
        ( B ) TYPE: nucleic acid ( C ) STRANDEDNESS: single
            ( D ) TOPOLOGY: linear ( x i ) SEQUENCE DESCRIPTION: SEQ ID NO:22:

GGGTTTTTAT TTTTAATTTT CTTTCAAATA CTTCCACCAT GGGTAACGGA TCCA             54

( 2 ) INFORMATION FOR SEQ ID NO:23:

( i ) SEQUENCE CHARACTERISTICS:
            ( A ) LENGTH: 58 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:23:

AGCTTGGATC CGTTACCCAT GGTGGAAGTA TTTGAAAGAA AATTAAAAAT AAAAACCC        58

( 2 ) INFORMATION FOR SEQ ID NO:24:

( i ) SEQUENCE CHARACTERISTICS:
            ( A ) LENGTH: 80 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:24:

CATGAACTTC CTCAAGAGCT TCCCCTTTTA TGCCTTCCTT TGTTTTGGCC AATACTTTGT      60

AGCTGTTACG CATGCTCGAG                                                  80

( 2 ) INFORMATION FOR SEQ ID NO:25:

( i ) SEQUENCE CHARACTERISTICS:
            ( A ) LENGTH: 79 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:25:

GATCCTCGAG CATGCGTAAC AGCTACAAAG TATTGGCCAA AACAAAGGAA GGCATAAAAG      60

GGGAAGCTCT TGAGGAAGT                                                   79

( 2 ) INFORMATION FOR SEQ ID NO:26:

( i ) SEQUENCE CHARACTERISTICS:
            ( A ) LENGTH: 32 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:26:

CTCTGGCAGT CCCCGCCTCG AGCCCCCTGC AG                                    32

( 2 ) INFORMATION FOR SEQ ID NO:27:

( i ) SEQUENCE CHARACTERISTICS:
            ( A ) LENGTH: 40 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:27:

GATCCTGCAG GGGGCTCGAG GCGGGGACTG CCAGAGCATG                            40

( 2 ) INFORMATION FOR SEQ ID NO:28:

( i ) SEQUENCE CHARACTERISTICS:

(A) LENGTH: 56 base pairs
(B) TYPE: nucleic acid
(C) STRANDEDNESS: single
(D) TOPOLOGY: linear ( x i ) SEQUENCE DESCRIPTION: SEQ ID NO:28:

CATGGCTCTA CAGCTCTGGC AGTCCCCGCC TCGAGGATAT CCTGCAGATC TCCCCA 56

( 2 ) INFORMATION FOR SEQ ID NO:29:

( i ) SEQUENCE CHARACTERISTICS:
(A) LENGTH: 56 base pairs
(B) TYPE: nucleic acid
(C) STRANDEDNESS: single
(D) TOPOLOGY: linear ( x i ) SEQUENCE DESCRIPTION: SEQ ID NO:29:

AGCTTGGGGA GATCTGCAGG ATATCCTCGA GGCGGGGACT GCCAGAGCTG TAGAGC 56

( 2 ) INFORMATION FOR SEQ ID NO:30:

( i ) SEQUENCE CHARACTERISTICS:
(A) LENGTH: 28 base pairs
(B) TYPE: nucleic acid
(C) STRANDEDNESS: single
(D) TOPOLOGY: linear ( x i ) SEQUENCE DESCRIPTION: SEQ ID NO:30:

AATTCAGATC TCCATGGATC GATGAGCT 28

( 2 ) INFORMATION FOR SEQ ID NO:31:

( i ) SEQUENCE CHARACTERISTICS:
(A) LENGTH: 20 base pairs
(B) TYPE: nucleic acid
(C) STRANDEDNESS: single
(D) TOPOLOGY: linear ( x i ) SEQUENCE DESCRIPTION: SEQ ID NO:31:

CATCGATCCA TGGAGATCTG 20